United States Patent [19]
Koizumi et al.

[11] Patent Number: 5,225,886
[45] Date of Patent: Jul. 6, 1993

[54] METHOD OF AND APPARATUS FOR DETECTING FOREIGN SUBSTANCES

[75] Inventors: Mitsuyoshi Koizumi; Yoshimasa Ohshima, both of Yokohama, Japan

[73] Assignee: Hitachi, Ltd., Tokyo, Japan

[21] Appl. No.: 584,120

[22] Filed: Sep. 18, 1990

[30] Foreign Application Priority Data

Sep. 18, 1989 [JP] Japan ................................. 1-239927
Sep. 18, 1989 [JP] Japan ................................. 1-239928

[51] Int. Cl.[5] .......................................... G01N 21/01
[52] U.S. Cl. ................................ 356/237; 356/338
[58] Field of Search ............... 356/237, 446, 336, 337, 356/338, 445

[56] References Cited
U.S. PATENT DOCUMENTS

| | | | |
|---|---|---|---|
| 3,790,287 | 2/1974 | Cuthbert et al. | 356/446 |
| 4,391,524 | 7/1983 | Steigmeier et al. | 356/237 |
| 4,740,079 | 4/1988 | Koizumi et al. | 250/572 |
| 4,806,774 | 2/1989 | Lin et al. | 356/237 |
| 4,889,998 | 12/1989 | Hayano et al. | 356/237 |

Primary Examiner—Richard A. Rosenberger
Attorney, Agent, or Firm—Antonelli, Terry, Stout & Kraus

[57] ABSTRACT

Disclosed herein are method of and apparatus for detecting a foreign substance on an object by illuminating said object, detecting via an optical system light reflected from said object and detecting said foreign substance in distinction from a background. The object is exposed to first illumination such that light reflected from said background is suppressed but light reflected from said foreign substance is highlighted relative to the light reflected from said background. The light reflected from said object as a result of said first illumination is detected, thereby obtaining a first detection signal. The object is exposed to second illumination such that light reflected from said background is free from suppression relative to the light reflected from said substance as a result of said second illumination. The light reflected from said object as a result of said second illumination is detected, thereby obtaining a second detection signal. Foreign-substance-highlighting processing is performed on said first detection signal by using said second detection signal, whereby said substance is detected.

21 Claims, 43 Drawing Sheets

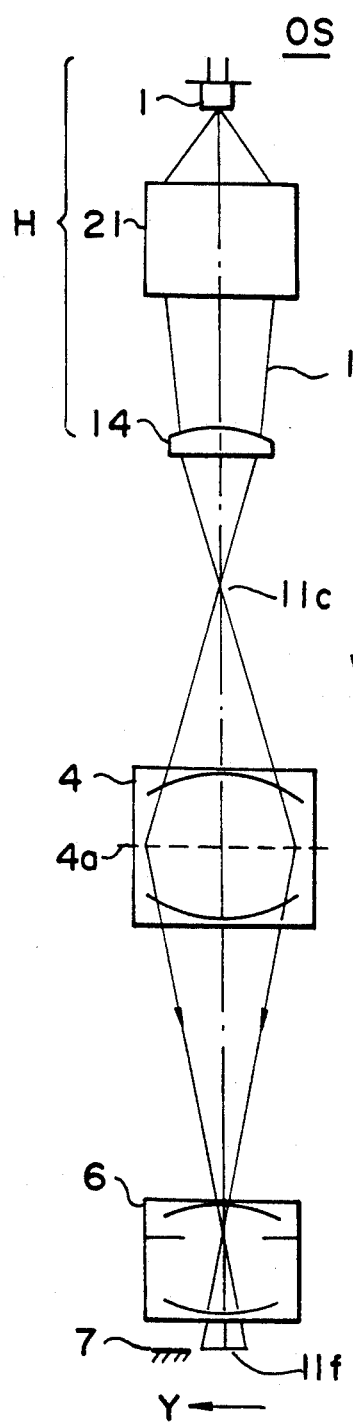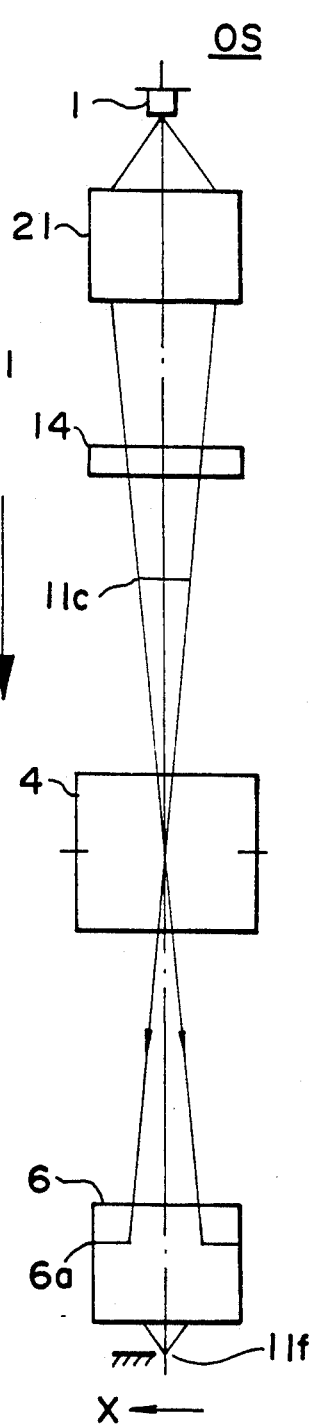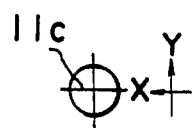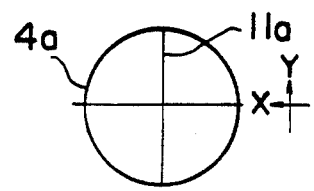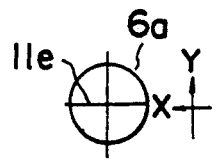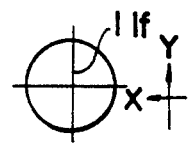

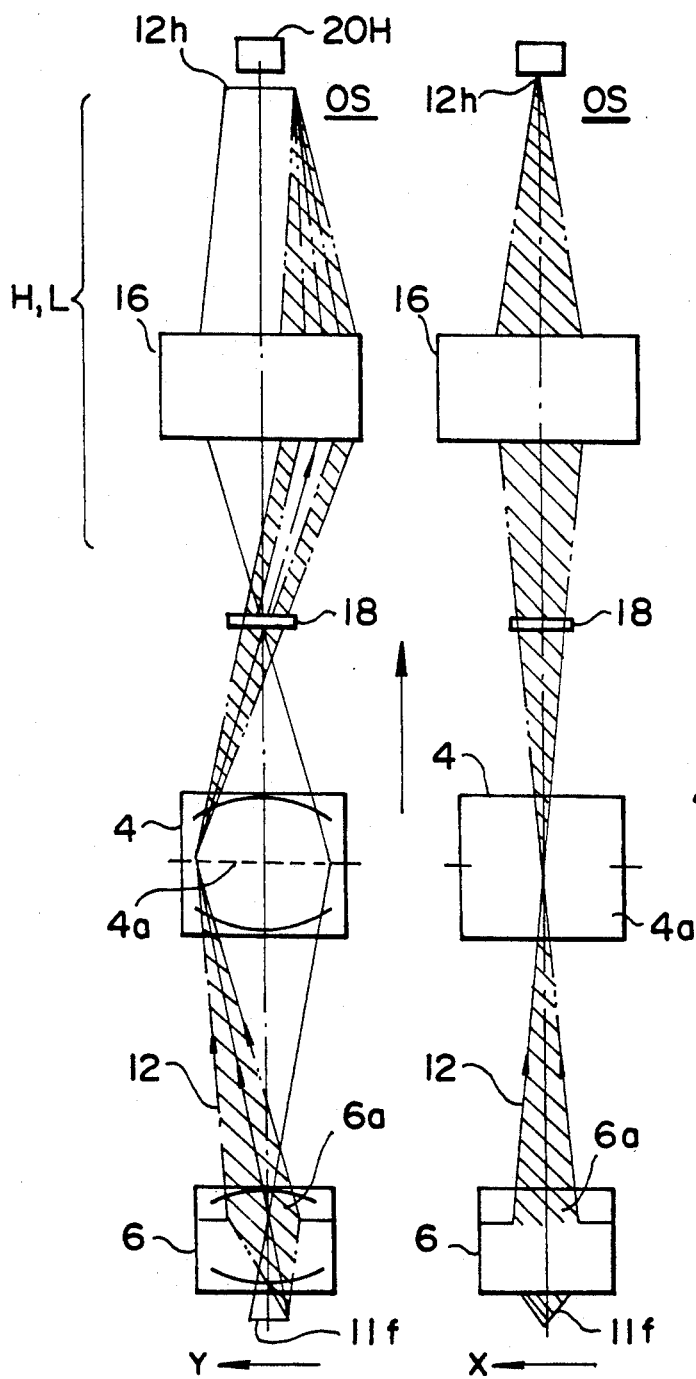

FIG. 13
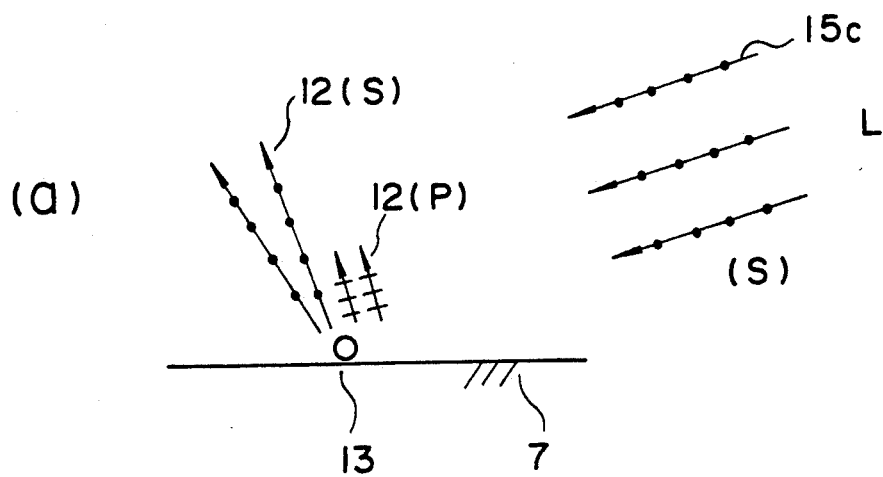
(a)
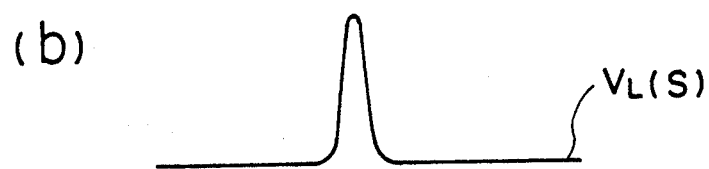
(b) $V_L(S)$
(c) $V_L(P)$
(d) $V_L(P+S)$

FIG. 16A

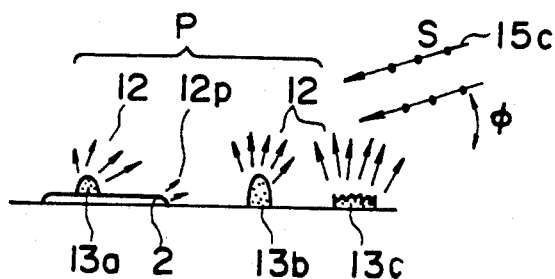

FIG. 16C

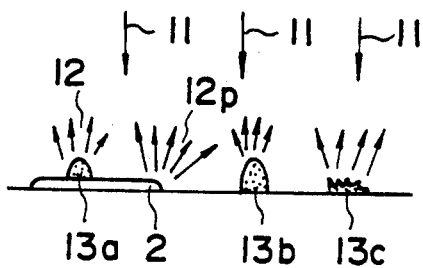

FIG. 16B

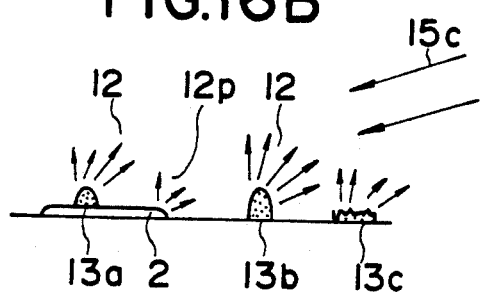

FIG. 16D

| | INCLINATION φ | | | | |
|---|---|---|---|---|---|
| | φ = 0~5° | | φ = 10~30° | | φ = 90° |
| | (A) | (B) | (A) | (B) | (C) |
| SCATTERED LIGHT 12p FROM PATTERN 2 | LOW | LOW | MEDIUM | MEDIUM | HIGH |
| | LOW (TOTAL) | | MEDIUM (TOTAL) | | |
| SCATTERED LIGHT 12 FROM FOREIGN SUBSTANCE 13a | MEDIUM | MEDIUM | MEDIUM | MEDIUM | MEDIUM |
| | MEDIUM (TOTAL) | | MEDIUM (TOTAL) | | |
| SCATTERED LIGHT 12 FROM FOREIGN SUBSTANCE 13b | MEDIUM | HIGH | MEDIUM | HIGH | MEDIUM |
| | HIGH (TOTAL) | | HIGH (TOTAL) | | |
| SCATTERED LIGHT 12 FROM FOREIGN SUBSTANCE 13c | HIGH | MEDIUM | HIGH | MEDIUM | MEDIUM |
| | HIGH (TOTAL) | | HIGH (TOTAL) | | |

FIG. 16E

| CONVENTIONAL EXAMPLE (2) | L | H | |
|---|---|---|---|
| INVENTION | L | | H |

FIG. 18

WAVELENGTH L:$\lambda 1$ , H:$\lambda 2$

| | CASE I | | | | CASE II | | | | CASE III | | | |
|---|---|---|---|---|---|---|---|---|---|---|---|---|
| | ILLUMI-NATION | | DETECTION | | ILLUMI-NATION | | DETECTION | | ILLUMI-NATION | | DETECTION | |
| | L | H | L | H | L | H | L | H | L | H | L | H |
| (a) | S | S | P | P | S | S+P | P | S+P | S+P | S | S+P | S+P |
| (b) | S | S | P | P+S | P | S+P | P | S+P | S+P | S | S | S |
| (c) | S | S | P | S | S | S+P | P | P | S+P | P | S+P | S+P |
| (d) | S | P | P | P | P | S+P | P | S+P | S+P | P | P | P |
| (e) | P | P | P | P+S | S | S+P | P | S | S+P | S+P | S+P | S+P |
| (f) | P | P | P | S | P | S+P | S | S | S+P | S+P | S | S |
| (g) | P | S | P | P+S | P | S+P | S | P | S+P | S+P | P | P |
| (h) | S | P | P | P+S | S | S+P | S+P | S+P | | | | |
| · | P | P | P | P | P | S+P | S+P | S+P | | | | |
| · | S | S | S | S | | | | | | | | |
| · | P | P | S | S | | | | | | | | |
| · | S | S | S+P | S+P | | | | | | | | |
| · | P | P | S+P | S+P | | | | | | | | |
| · | S | P | S+P | S+P | | | | | | | | |
| · | P | S | S+P | S+P | | | | | | | | |
| · | P | S | S | S | | | | | | | | |
| · | P | S | P | P | | | | | | | | |

FIG. 24A
PRIOR ART
FIG. 24C
PRIOR ART
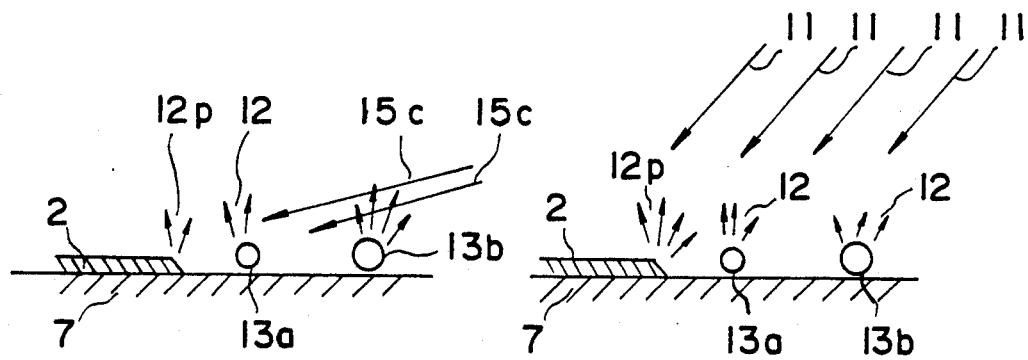
FIG. 24B
PRIOR ART
FIG. 24D
PRIOR ART
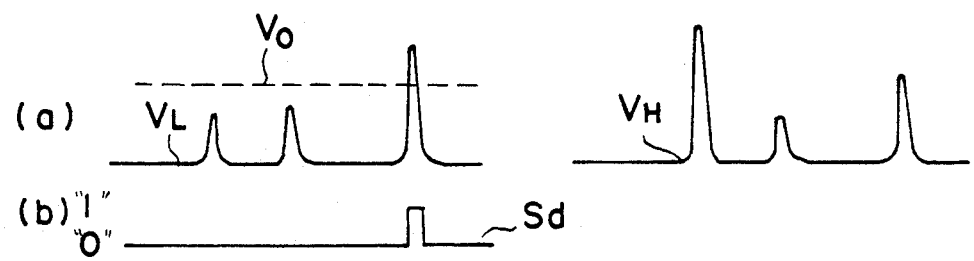
FIG. 24E
PRIOR ART
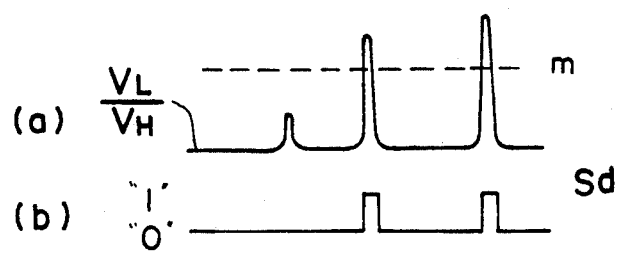

FIG.26A
PRIOR ART
FIG.26C
PRIOR ART
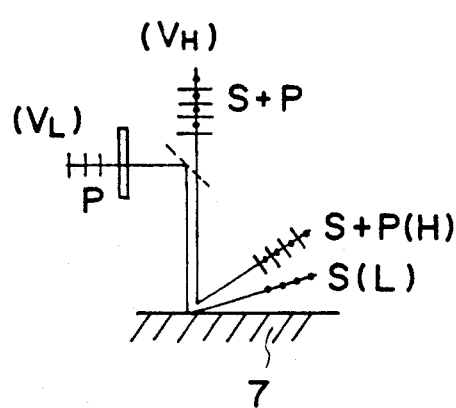
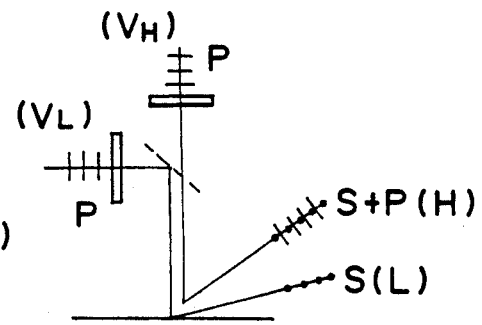
FIG.26B
PRIOR ART
FIG.26D
PRIOR ART
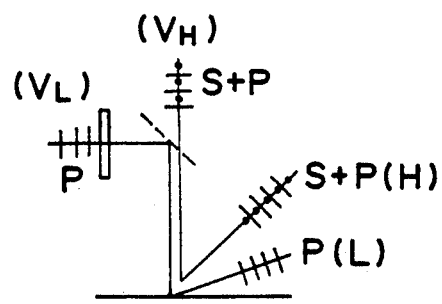
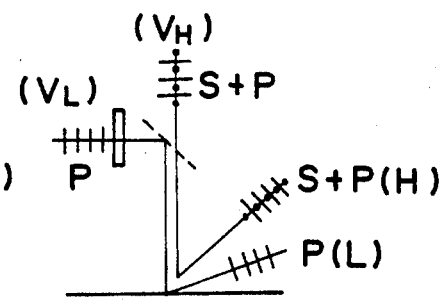

METHOD OF AND APPARATUS FOR DETECTING FOREIGN SUBSTANCES

BACKGROUND OF THE INVENTION a. Field of the Invention

The present invention relates to a method of and apparatus for detecting one or more foreign substances on a semiconductor LSI wafer or a mask pattern, and especially to a method and apparatus suitable for the high-speed and high-sensitivity detection of one or more fine foreign substances on a patterned wafer or the like in an intermediate step of an LSI fabrication process.

b. Description of Related Art:

Inspection of foreign substances on a patterned wafer in an intermediate step of an LSI fabrication process is indispensable for the improvement of yield and reliability. Conventional methods and apparatus for the automatic detection of foreign substances on a patterned wafer were realized using a detection technique which makes use of polarized light as disclosed in Japanese Patent Application Laid-Open Nos. 149829/1980, 101390/1979, 94145/1980 and 30630/1981. The principle of this detection technique will next be described with reference to FIGS. 21A, 21B and 21C and FIGS. 22A and 22B.

FIGS. 21A, 21B and 21C are schematic illustrations of the principle of detection of a foreign substance by a first example of the conventional methods for the detection of foreign substances and an apparatus therefor. An S polarized laser beam 15c is irradiated horizontally onto a wafer 7 as shown in FIG. 21A. Light 12p is then reflected without any change in polarization from a pattern 2 on the wafer 7, said pattern 2 extending at a right angle to the illumination beam 15c and advances, still in the S polarized state, to an object lens 6. An analyser 151 is arranged with its axis of polarization extending perpendicularly to the polarization of the reflected light 12p, so that the reflected light 12p is subjected to extinction and is not allowed to reach a detector 20. In the case of light 12p reflected from the pattern 2 which extends at an angle with respect to the illumination beam 15c as shown in FIG. 21B, the light 12p does not enter the object lens 6 and is not detected. When the illumination beam 15c which is travelling in a Y direction is irradiated onto a foreign substance 13 on the wafer 7 as depicted in FIG. 21C, the polarization of the illumination beam is changed and reflected light 12 is produced as P polarized light (a sort of elimination phenomenon of polarization). Since the P polarized light can pass through the analyser 151, the foreign substance 13 can be detected by the detector 20.

FIGS. 22A and 22B are a perspective view and discrimination ratio graph of an optical system in the first example of the conventional methods and apparatus for the detection of foreign substances. When the oblique angle $\phi$ of the S polarized laser beam 15c from a laser beam source 15 is successively changed relative to the wafer 7, there is obtained a graph of measurement data of discrimination ratio which is the ratio of the intensity of the light 12 scattered by a 0.5 μm foreign substance of 1 μm foreign substance to the intensity of the light 12p scattered by the pattern, said foreign-substance-scattered light 12 and said pattern-scattered light 12p being both detected by the detector 20 via the object lens 6 and the analyser 151, as shown in FIG. 22B. Using the variations in the output characteristics of the foreign substance 13 and the pattern 2 according to the oblique angle $\phi$, the oblique angle $\phi$ is changed in a suitable range, followed by detection and comparison.

According to a second example of the conventional methods and apparatus for the detection of foreign substances on a patterned wafer, as illustrated in U.S. Pat. No. 4,740,079 issued Apr. 26, 1988, to the present assignee and incorporated herein by reference, not only polarized laser illumination having a large scattering loss but also illumination having a small scattering loss, namely, two types of illumination are applied to a foreign substance. Making use of the fact that the former illumination tends to produce scattered light at the foreign substance while the latter illumination tends to give off scattered light at the pattern, fine foreign substances can each be detected more stably with higher sensitivity by detecting the ratio of a signal corresponding to the former scattered light to a signal associated with the latter scattered light. The second example uses plural photoelectric solid pickup element arrays of the type where the size of each of the pixels of their light-receiving portions is on the order of 5×5 μm² as converted to the corresponding value on the surface of a sample. Signals outputted from the individual elements are subjected to concurrent comparison processing, whereby high-sensitivity detection of foreign substances can be achieved without deterioration of high-speed performance. The principle of this detection method for foreign substances will next be described with reference to FIGS. 23 through 26D.

FIG. 23 is a perspective view of an optical system according to the second example of the conventional methods and apparatus for the detection of foreign substances. The conventional method depicted in FIG. 23 uses variations in the output characteristics of the foreign substance 13 and pattern 2 according to the oblique angle $\phi$ shown in FIGS. 22A and 22B. For example, a low-angle S-polarized illumination beam 15c (wavelength: $\lambda_1$) from a laser light source 15L and a condenser lens 15bL and a high-angle S-polarized illumination beam 11 (wavelength: $\lambda_2$) from a laser light source 15H and a condenser lens 15bH are irradiated onto the same point on the sample. Of light reflected from the point, a P polarization component of scattered light 12 obtained by way of the object lens 6, a color-separation prism 150 and detection elements 151L,151H is solely detected by photoelectric solid pickup element arrays 20L,20H. Their output signals $V_L,V_H$ are compared at analog division comparators 100 and then converted to binary signals at binarizing circuits 101. The binary signals are then outputted through an OR gate/OR circuit 22.

FIGS. 24A through 24E are schematic illustrations of output signals and the like in FIG. 23. FIG. 24A is a side view showing the scattered lights 12p,12 occurring upon irradiation of the laser beam 15c at a lower oblique angle onto the sample (Si wafer) 7 having thereon the pattern (POLY-Si) 2 and the foreign substances 13a,13b of different sizes. FIG. 24B(a) shows the waveform of the output signal $V_L$ at that time, while FIG. 24B(b) depicts the waveform of a binary signal Sd obtained in accordance with a threshold value $V_O$. FIG. 24C is a a side view in which the laser beam 11 is irradiated at a higher oblique angle onto the sample (Si wafer) 7 having thereon the pattern 2 and the foreign substances 13a,13b. FIG. 24D illustrates the waveform of the output signal $V_H$ at that time. Further, FIG. 24E(a) shows the waveform of the output signal ratio $V_L/V_H$ and FIG. 24E(b) depicts the waveform of the binary signal Sd obtained in accordance with a threshold value m.

FIGS. 25A through 25H and FIGS. 26A through 26D are optical path diagrams of the polarization in FIG. 23. fig. 25A shows the above illumination and detection conditions in a simplified schematic manner. The output signals $V_L$ and $V_H$ are obtained as a result of detection of the P polarized components of scattered lights S(L) and S(H), which have been obtained upon irradiation of the sample 7 by the S-polarized illumination beams 15c,11, by the color-separation prism 150 and the analysers 151L,151H. The illumination and detection conditions are not limited to the conditions depicted in FIG.25A but various illumination and detection conditions as shown in FIGS. 26A through 26D are also usable. In these drawings, the illumination and detection conditions L for highlighting the foreign substances 13a,13b can be either the detection of the P-polarized component by the S-polarized illumination S(L) or the detection of the P-polarized component by the P-polarized illumination P(L). Reasons for this are set out in U.S. Pat. No. 4,740,079 referred to above.

On the other hand, the illumination and detection conditions H for highlighting the pattern 2 can be any conditions other than both the above illumination and detection conditions L, so that it is not absolutely necessary to use polarized light by laser beam illumination. Namely, incoherent light such as that available from the use of a conventional halogen lamp or the like can be employed. This light is indicated by S+P in FIGS. 26A through 26D.

As the above color-separation prism 150, it is possible to use the dichroic prism (or mirror) disclosed in Japanese Patent Application Laid-Open No. 149829/1980 or 43559/1981 or a combination of a light-splitting prism (semitransparent mirror) and a color filter or interference filter. When the laser beam sources 15L,15H are two lasers of different wavelengths selected from He-Ne laser (λ: 6,328 Å), GaAlAs laser diodes (λ: 7,800–8,300 Å), InGaAsP laser diode (λ: 13,000 Å) and Ar laser (λ: 4,580 Å, for example), their laser beams can be condensed on the surface of the sample 7. As a result, high illuminance can be obtained so that the detection of the scattered lights 12p, 12 can be stabilized further. As has been described above, it is the essential requirement for the second example of the conventional art that the illumination and analysis conditions L for highlighting foreign substances are either the detection of P polarized light component by the S-polarized illumination S(L) or the analysis of P polarized light component by the P-polarized illumination P(L) and the foreign-substance-highlighting illuminations L have a wavelength $\lambda_1$ or $\lambda_2$ different from that of the pattern-highlighting illumination H.

FIG. 27 is a detailed circuit diagram of a signal processing circuit which contains the analog division comparators of FIG. 23. In FIG. 27, output signals $V_L,V_H$ from the detectors 20L,20H are processed pixel by pixel i-n at the analog division comparators 100 so that output signal ratios $V_L/V_H$ are calculated. At the binarizing circuits 101, these output signal ratios are converted to binary signals in accordance with the threshold value m. The OR gate 22 carries out the logic OR between the corresponding binary signals from the binarizing circuits 101. Whenever the logic OR results in "1", it is stored in a foreign substance memory 23. The analog comparison method of FIG. 23 (FIG. 27) will next be described in further detail with reference to FIG. 28A through FIG. 30B.

FIGS. 28A, 28B and 28C schematically illustrate the experimental results under the illumination and analysis conditions shown in FIG. 23. FIGS. 28A and 28B are plan and side views of the reflected lights (scattered lights) 12p,12 from the circuit pattern 2 and foreign substance 13 on the sample 7 when illuminated by the beams 15c,11, respectively. FIG. 28C is a diagrammatic representation of the experimental data, in other words, the relation between the output signals $V_L$ and $V_H$ under the above conditions. Incidentally, the object lens 6 is provided with a lens frame 6a in FIG. 28B. With respect to the scattered light 12p from the pattern 2, the output signals $V_L,V_H$ of the scattered light 12p from the pattern 2 are measured while successively turning the pattern 2 over angles η from an angular point perpendicular to the projecting direction of the illumination beams 15c,11 onto the surface of the sample wafer 7. Using standard particles of 0.5, 0.7, 1 and 2 μm (no turning is needed in this case), the output signals $V_L,V_H$ of the scattered lights 12 from the foreign substance 13 are measured. FIG. 28C diagrammatically illustrates the experimental data, i.e., the relation between the output signals $V_L$ and $V_H$. It is understand from this diagram that the, at any desired angles η of the pattern 2, the output signal ratios $V_L/V_H$ (indicated by circles) from the pattern 2 are smaller than the threshold value m of a discrimination threshold line $V_L/V_H = m$ (the inverse of the inclination of the broken line in the diagram) but the output signal ratios $V_L/V_H$ (indicated by dots) from the standard particles of 0.7-2 μm and an actual larger foreign substance U as the foreign substance 13 are greater than the threshold value m of the discrimination threshold line. The sample wafer 7 was turned successively over the angles η, because the sample wafer 7 has on the surface thereof the pattern 2 extending at various angles η and the foreign substance 13 must be stably detected in distinction from the pattern 2.

With reference to FIGS. 29A through 30B, a description will next be made of a method for discriminating the pattern 2 and the foreign substance 13 from each other by means of an electric circuit which has been constructed by taking into consideration the characteristics of the output signals $V_L$, $V_H$ from the pattern 2 and the foreign substance 13 depicted in FIG. 28C.

FIG. 29A is a characteristic diagram of the output signal ratios $V_L/V_H$ illustrated in FIG. 28C. FIG.29B is a circuit diagram showing an exemplary discriminator which makes use of the analog division comparator 100 and is adapted to realize the characteristics of the output signal ratios $V_L/V_H$ shown in FIG. 29A. The output signals $V_L,V_H$ are processed at the analog division comparator 100, so that the output signal ratio $V_L/V_H$ is calculated. At the binarizing circuit 101, the ratio is then converted to a binary signal on the basis of the threshold value m and, when the output signal ratio $V_L/V_H$ is greater than m, "1"* is outputted. When the output signal $V_H$ is low, the calculation error of the output signal ratio $V_L/V_H$ becomes larger so that the calculation results become unstable (for example, $V_L/V_H = \alpha$ when $V_H$ is zero). As a method for overcoming this problem, it is only necessary to set the calculation results of the output signal ratio $V_L/V_H$ effectively at "1" whenever $V_L > V_{TH}$, $V_{TH}$ being the value of an output signal $V_L$ corresponding to the foreign substance 13 as large as 0.5 μm, in FIG. 29A. This can be realized by a binarizing circuit 104 for the output signal $V_L$, said binarizing circuit 104 having a threshold value $V_{TH}$, and an AND gate 103 having inputs "1"* and "1"**.

FIG. 30A is a characteristic diagram of differences $V_L - V_H$ of the output signals shown in FIG. 28C. FIG. 30B is a circuit diagram of an illustrative discriminator which uses an analog subtraction comparator 105 for obtaining the characteristics of the output signal differences $V_L - V_H$ of FIG. 30A. In this case, the discrimination threshold line is set at m=1 (inclination: 45°) by adjusting the intensity of either one of the illumination beams 15c, 11 by the illuminations L,H and/or the gain of an unillustrated output amplifier of either one of the pickup element arrays 20L,20H. Whenever the output from the binarizing circuit 104 is "1"** ($V_L > V_m$), the output "1"* of the subtraction result $V_L - V_H$ from the analog subtraction comparator 105 for the output signals $V_L, V_H$ of FIG. 30B is outputted as an effective "1" from the AND gate 103. Incidentally, instead of the analog division or subtraction comparison shown in FIG. 29B through 30B, the output signals $V_L, V_H$ can be subjected to digital calculation after they have been subjected to A/D conversion.

It is the overlooking of foreign substances that is involved as a first problem in the second example of the prior art. To detect the 0.5 μm foreign substance in distinction from the pattern on the basis of the measurement results of FIG. 22B, it is desirable to set the oblique angle φ of the illumination L at about 0°-5° degrees and the oblique angle φ of the illumination H at 10° or greater and to compare signals of scattered lights. To detect 0.5 μm foreign substances at a high S/N ratio, an object lens 6 having a diameter large enough to permit effective condensing of scattered light is required. The lens frame 6a of FIG. 28B therefore becomes large. As a result, oblique angles φ of 10° lead to interference of the illumination beam 11 with the lens frame (metal frame) 6a so that no sufficient discrimination performance can be obtained. As a result, the 0.5 μm foreign substance shown in FIG. 28C is overlooked. The foregoing are the experimental data obtained by using, as models of foreign substances, spherical particles called standard particles. The actual foreign substance Q of the submicron order shown in FIG. 28C is also overlooked.

It is a lack of sufficient intensity by light scattered from a foreign substance that is involved as a second problem in the second example of the prior art. As will be described subsequently with reference to FIG. 13(a), where the illumination beam 15c from the oblique illumination L for highlighting the foreign substance 13 is an S-polarized beam, it is only the P-polarized component 12(P) out of the light 12 scattered from the foreign substance that is detected by the detector 20L in the second conventional example. Because the P-polarized component 12(P) is considerably smaller than the S-polarized component 12(S) retaining its polarized state, it is impossible to obtain any sufficient quantity of light at the detector 20L. It is therefore impossible to obtain any sufficient S/N ratio for the output signal $V_L$(P) shown in FIG. 13(c). Low-pass filtering is hence applied to the output signal $V_L$ to reduce the noise N, so that a long time is required for the detection of the foreign substance.

It is a lack of sensitivity for fine foreign substances on a mirror-finished surface that is involved as a third problem in the second example of the prior art. For the detection of foreign substances on an LSI wafer or the like, it is generally required to be able to detect not only foreign substances of 0.5 μm and greater on the pattern but also foreign substances of 0.1 μm and greater on the mirror-finished surface and the mirror-finished film. As will be described subsequently with reference to FIGS. 14A and 14B, in the case of a foreign substance 13 of the submicron order, forward scattered light 12f is strong but side scattered light 12e impinging upon the object lens 6 is weak, in the light 12 scattered from the foreign substance upon exposure to the low-angle illumination beam 15c(11). It is therefore desirable to enlarge the angular aperture of the object lens 6 with a view toward detecting a part of the forward scattered light 12f. For the reasons described above in connection with the first problem, however, a limitation is imposed on the size of the angular aperture α. No sufficient quantity of light can therefore be obtained from 0.1 μm foreign substances on a mirror-finished sample, whereby the output signal $V_L(V_H)$ shown in FIG. 13(b) cannot be detected.

If the points of detection by the two detectors 20L,20H on a sample are not registered in the second example of the prior art as depicted in FIG. 41, the detectors may not use corresponding pixels to detect the pattern 2 and the foreign substances 13a,13b or the timing of detection by a pixel of one of the detectors may not coincide with the timing of detection by the corresponding pixel of the other detector. This may lead to a deterioration in the detection sensitivity for foreign substances. To avoid these problems, precise positional or sensitivity matching is needed between the two detectors 20L and 20H. Obviation of such positional or sensitivity matching, if feasible, is believed to lead to simplification of detection procedures for foreign substances.

Further, the detectors 20L,20H are employed in the second example of the prior art so that an amplifier and the like are required for each of the detectors. If detection is feasible by using only one detector, the circuit size can be reduced correspondingly. This is certainly preferable.

SUMMARY OF THE INVENTION

A first object of the present invention is to provide a method of and apparatus for detecting at a high speed fine foreign substances of about 0.5 μm on a patterned sample in distinction from the pattern.

A second object of the present invention is to provide a method of and apparatus for detecting at a high speed foreign substances of about 0.1 μm on a mirror-finished surface.

A third object of the present invention is to provide a method of and apparatus for detecting foreign substances, which method and apparatus can achieve both the first object and the second object by substantially the same constitution.

A fourth object of the present invention is to provide a method of and apparatus for detecting foreign substances, which method and apparatus permit omission of positional or sensitivity matching of detectors and also a reduction in the circuit size.

To achieve the first object, according to a first embodiment of the present invention, each foreign substance on an object is exposed to two types of illumination, one being oblique illumination which is irradiated obliquely onto the object from the outside of an object lens of an optical system and has a large scattering loss and the other being vertical illumination which is irradiated onto the object through the object lens of the optical system and has a small scattering loss. In view of the fact that scattered light from the oblique illumination tends to occur at the foreign substance but scattered light from the vertical illumination tends to occur at a pattern, the ratio of signals corresponding to the scattered lights by the two types of illuminations is detected so that fine foreign substances on a patterned object can be detected more stably and with higher stability.

To attain the second object, according to a second embodiment of the present invention, fine foreign substances on a mirror-finished surface can be detected at high speed and with high sensitivity by producing weak scattered light from the fine foreign substances from the vertical illumination in such a way that the weak scattered light can be effectively condensed by a detection system.

To fulfill the third object, there is provided a system according to a third embodiment of the present invention, which is capable of detecting fine foreign substances on a patterned object and capable of detecting fine foreign substances on a mirror-finished surface at high speed and with high sensitivity, by changing beam sources and/or other components, using a change-over means.

To achieve the fourth object, according to a fourth embodiment of the present invention, foreign substances on an object can be detected by alternately performing first and second illuminations in a time-sharing manner and alternately detecting, by a single photoelectric element, light scattered from the object in synchronization with the first and second illuminations.

According to the present invention, high oblique-angle illumination is irradiated as vertical illumination H in addition to oblique illumination L. As will be described subsequently with reference to FIGS. 15A–17, the discrimination threshold value m between a foreign substance and a pattern for the ratio $V_L/V_H$ of a signal corresponding to light scattered from the oblique illumination L to a signal corresponding to light scattered from the vertical illumination H can therefore be rendered smaller. As a result, the discrimination performance for fine foreign substances and a pattern can be improved. Further, as will also be described later with reference to FIG. 13, strong scattered light in which the polarization of the oblique illumination L is retained unchanged can be used, so that stronger scattered light signals $V_L$ can be obtained and high-speed inspection is hence feasible.

By using vertical illumination H as the high oblique-angle illumination in addition to the oblique illumination L in accordance with the present invention, light scattered from fine foreign substances of the submicron order can be effectively condensed as will be described later with reference to FIGS. 14C and 14D. Strong scattered light signals $V_H$ can therefore be obtained, thereby permitting high-speed and high-sensitivity detection of fine foreign substances on a mirror-finished surface.

The third object is also attained by using a system which is capable of conducting high-speed and high-sensitivity detection of fine foreign substances on a pattern and of fine foreign substances on an associated mirror-finished surface with a switching means for a signal processing circuit for processing scattered light signals $V_L, V_H$ from the first and second foreign substance detectors.

The above foreign-substance detection method and apparatus can be free from deterioration of the detection sensitivity for foreign substance, as the first illumination (oblique illumination) and the second illumination (vertical illumination) are performed in a time-sharing pulse-like manner and the detection of light scattered as a result of illumination by the first illumination (oblique illumination) and that of light scattered as a result of illumination by the second illumination (vertical illumination) can be conducted by the same photoelectric element (detector) in synchronization with the first and second illuminations, respectively.

Incidentally, the above time-sharing illumination and detection can be applied irrespective of whether the second illumination is vertical illumination or not. This method can therefore be applied, for example, to the above-described second example of the prior art.

BRIEF DESCRIPTION OF THE DRAWINGS

FIG. 2A through FIG. 2F are simplified schematic side views, plan views and partial cross-sectional views of an optical path of a vertical illumination system in the first embodiment depicted in FIG. 1;

FIG. 3A through FIG. 3F are simplified schematic side views, plan views and partial cross-sectional views of an optical path of a scattered light detection system in the first embodiment illustrated in FIG. 1;

FIG. 13 schematically depicts polarization characteristics of scattered lights by oblique illumination in FIG. 1 through FIG. 12;

FIG. 16A through FIG. 16E schematically show the intensities of scattered light in FIG. 1 through FIG. 12;

FIG. 18 shows polarizations usable in the respective embodiments of the present invention;

FIG. 24A through FIG. 24E schematically show output signals, etc.;

FIG. 25A through FIG. 25H and FIG. 26A through FIG. 26D are optical path diagrams of the polarizations in FIG. 23;

DETAILED DESCRIPTION OF THE INVENTION AND PREFERRED EMBODIMENTS

Figure 1:
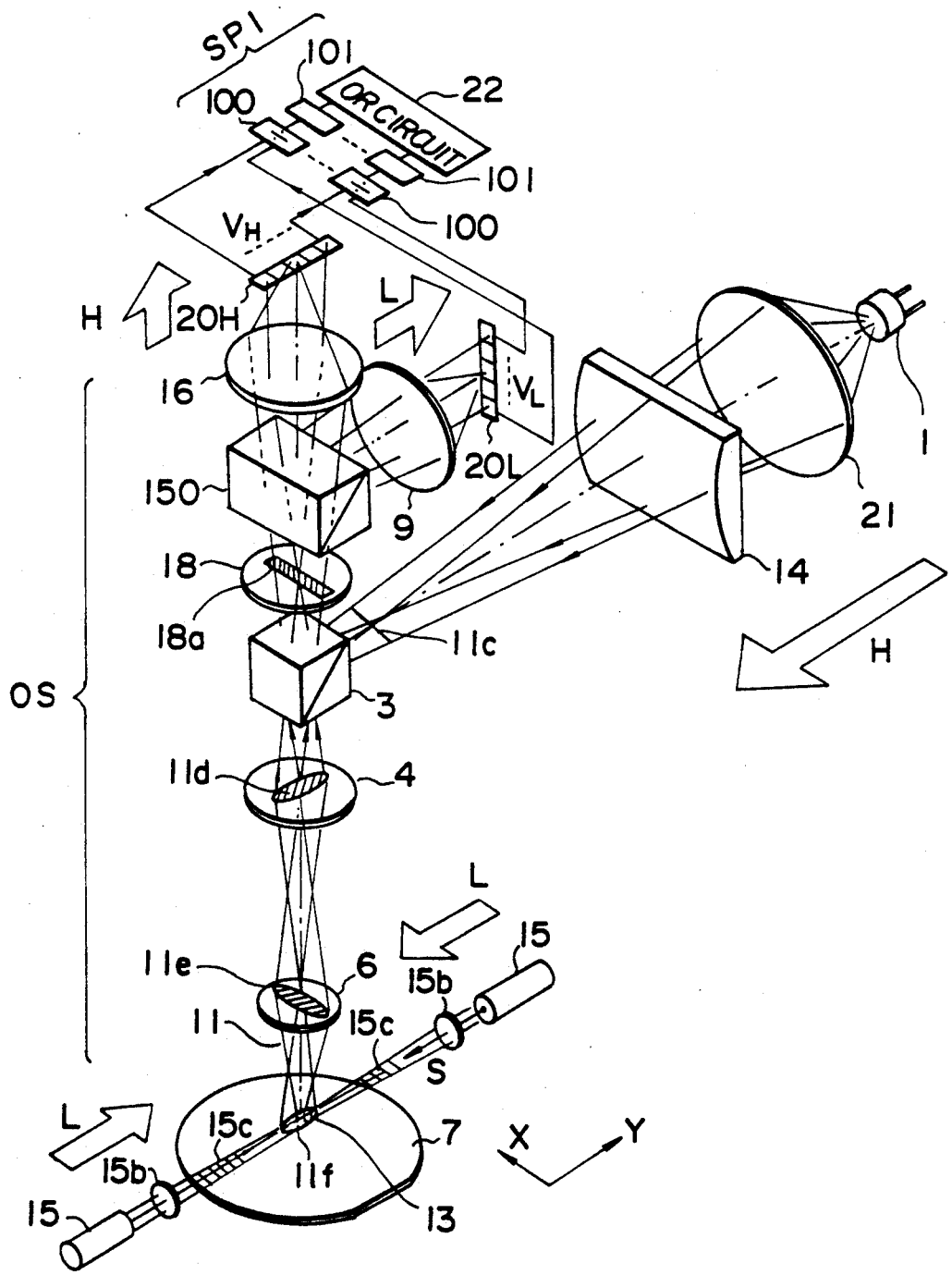
FIG. 1 is a perspective view of an optical system, showing a first embodiment of the present invention.

The embodiments of the present invention will hereinafter be described with reference to the accompanying drawings.

In the following embodiments, like elements of structure will be identified by like reference numerals and overlapping descriptions will be omitted.

FIG. 1 shows a foreign-substance-detecting method and apparatus according to a first embodiment of the present invention which are suitable for the detection of foreign substances on an object such as a patterned wafer. The construction of illumination and detection systems are primarily illustrated in FIG. 1.

The foreign-substance-detecting apparatus of the first embodiment is adapted to detect foreign substances on the object in distinction from a background of a surface of the object. The apparatus is equipped with an oblique illumination system L capable of functioning as a first illumination means for performing illumination such that light reflected from the background is suppressed but light reflected from each foreign substance is highlighted relative to the light reflected from the background, a vertical illumination system H capable of functioning as a second illumination means for performing illumination such that light reflected from the background is free from suppression relative to the light reflected from each foreign substance as a result of said second illumination, a detection system L capable of functioning as a first detection means for detecting the light reflected from the object as a result of illumination by the oblique illumination system L to obtain a detection signal, another detection system H capable of functioning as a second detection means for detecting the light reflected from the object as a result of illumination by the vertical illumination system H to obtain another detection signal, an optical system OS for guiding the light reflected from the object to the detection system L and the detection system H, and a signal processing means SP1 for performing foreign-substance-highlighting processing on the detection signal from the detection system L by using the detection signal from the detection system H. Although not shown in FIG. 1, the apparatus is also provided with a stage for carrying the object thereon, a drive mechanism for moving, for example, shifting or turning the stage, and the like as will be described subsequently.

In FIG. 1, the oblique illumination system L for performing illumination onto the sample substrate 7 in an oblique direction is composed of two pairs of a laser beam source 15 and a condenser lens 15b. As the case may be, one pair may suffice. On the other hand, the vertical illumination system H adapted to conduct linear (slit-like) vertical illumination onto the sample substrate 7 is composed of a laser beam source 1, a condenser lens 21, a cylindrical lens 14, a semitransparent prism 3, a field lens 4 and an object lens 6. In the detection system L for the oblique illumination, light reflected by a color-separation prism 150 is formed into an image by an imaging lens 9 and is then detected by the one-dimensional solid pickup element array (detector) 20L. The detection system H for the vertical illumination comprises a light shutoff plate 18 having a light shutoff portion 18a for shutting off zeroth-order diffracted light, an imaging lens 16, and a one-dimensional solid pickup element array (detector) 20H. The detectors 20L, 20H are connected to their corresponding drivers for driving and controlling the detectors, although the drivers are not shown in the drawing. Output signals $V_L, V_H$ detected by the detectors 20L, 20H are inputted to and processed by a signal processing means SP1. The signal processing means SP1 is constructed of analog division comparators 100, binarizing circuits 101, and OR gate 22. The vertical illumination system H eliminates the need for a means for scanning the sample 7 in the Y direction as the cylindrical lens 14 is provided as an optical element for effecting one-dimensional convergence and the laser illumination beam 11 is condensed into a linear spot 11f on the sample 7. The optical path of the vertical illumination system H will next be described with reference to FIGS. 2A through 2F.

FIG. 2A, FIG. 2B and FIGS. 2C through 2F are a side view, a plan view and partly cross-sectional views of the optical path of the vertical illumination system H without the semitransparent prim 3 in FIG. 1, respectively. In the vertical illumination system of FIG. 2A through FIG. 2F, after the laser beam 11 emitted from the laser beam source 1 through the condensing lens 21 (see FIGS. 2A and 2B) has passed through the cylindrical lens 14, a linear laser spot 11c is formed as shown in FIG. 2C. After being reflected by the semitransparent prism 3, the laser beam 11 forms a linear spot 11d in a diaphragm 4a of the field lens 4. Thereafter, a linear spot 11e is formed in a diaphragm 6a of the object lens 6 as depicted in FIG. 2E. After passage through the object lens 6, the linear spot 11f is condensed on the sample 7 as indicated in FIG. 2F. When there is no foreign substance 13 on the sample 7 under illumination by the vertical illumination system H, the reflected light 11 from the sample substrate 7 returns along exactly the same light path and reaches the semitransparent prism 3. The reflected light 11 which has passed through the semitransparent prism 3 is then shut off by the linear shutoff portion 18a of the shutoff plate 18 arranged in the optical path of the vertical illumination detection system H of FIG. 1. Assume that the foreign substance 13 on the sample 7 is present at an end of the linear spot 11f. An optical path and imaging of the scattered light 12 from the foreign substance 13 will next be described with reference to FIGS. 3A through 3G.

FIG. 3A, FIG. 3B and FIGS. 3C through 3G are a side view, a plan view and partly cross-sectional views of the optical paths of the detection systems H,L which are shown in FIG. 1 and are adapted to detect scattered light 12 from the foreign substance 13 on the sample 7. The semitransparent prism 3 is omitted. In FIG. 3A through FIG. 3F, the scattered light 12 (see FIG. 3A and 3B) from the end of the linear spot 11f depicted in FIG. 3G at which end the foreign substance 13 on the sample 7 is located forms a spread 12c extending over the entire area of the diaphragm 6a of the object lens 6 as shown in FIG. 3F. After passage through the object lens 6, an image 12d of the scattered light is formed in the diaphragm 4a of the field lens 4 as illustrated in FIG. 3E. The scattered light 12 which has passed through the semitransparent prism (see FIG. 1) in the vertical illumination system H travels through the light shutoff plate 18 and the color-separation prism 150 (see FIG. 1). It is then formed by the imaging lens 16 into an image 12h on the detector 20H as shown in FIG. 3C. All the scattered light 12 passes through a transparent portion outside the linear shutoff portion 18a (see FIG. 3D) of the shutoff plate 18, because the scattered light 12 is diffracted light of at least the first order and its spread 12i is distributed outside the linear shutoff portion 18a in which the zeroth scattered light, i.e., the reflected light 12 from the surface of the sample 7 is distributed. On the other hand, the reflected light 12 which has passed through the semitransparent prism 3 in the oblique illumination system L is reflected by the color-separation prism 150 and, by the imaging lens 9 arranged in the optical path of the oblique illumination detection system L, is formed into an image on the detector 20L. Examples of polarizations of the illumination beam 11 and the scattered light 12 in FIG. 1 will next be described with reference to FIG. 4 through FIG. 6.

Figure 4:
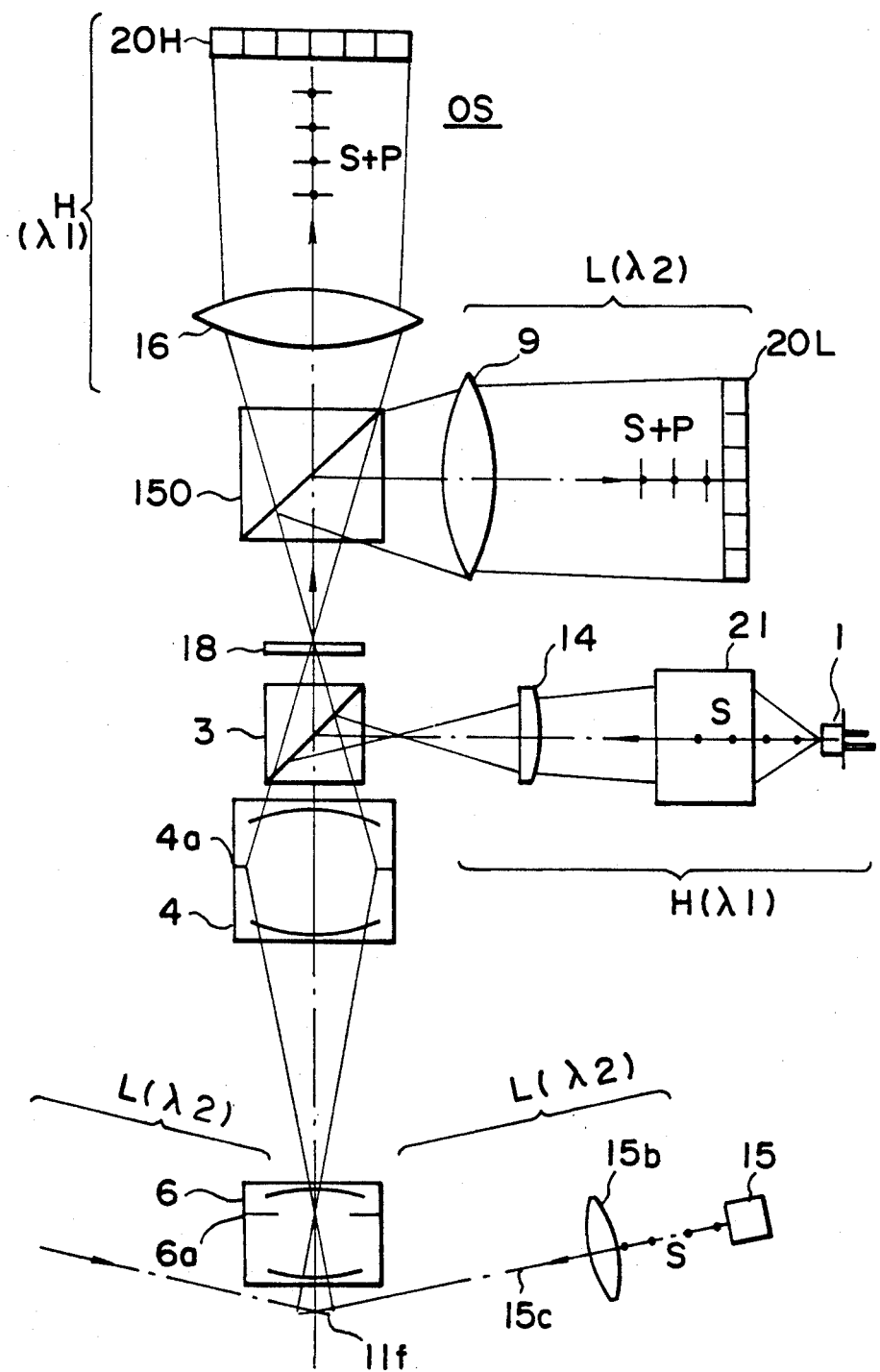
FIG. 4, FIG. 5 and FIG. 6 are optical path diagrams of three types of polarization in the optical system of FIG. 1.
Figure 5:
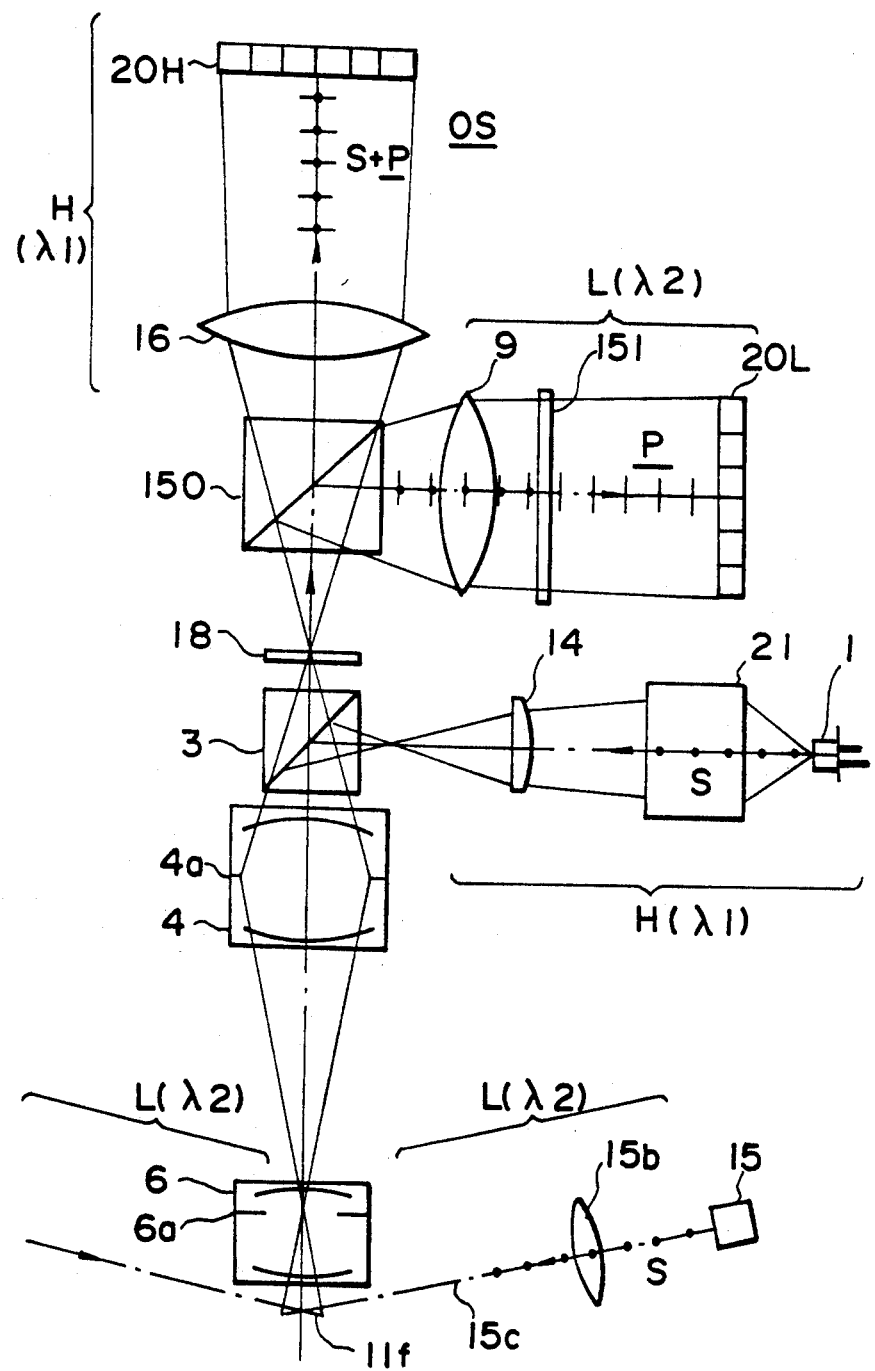
Figure 6:
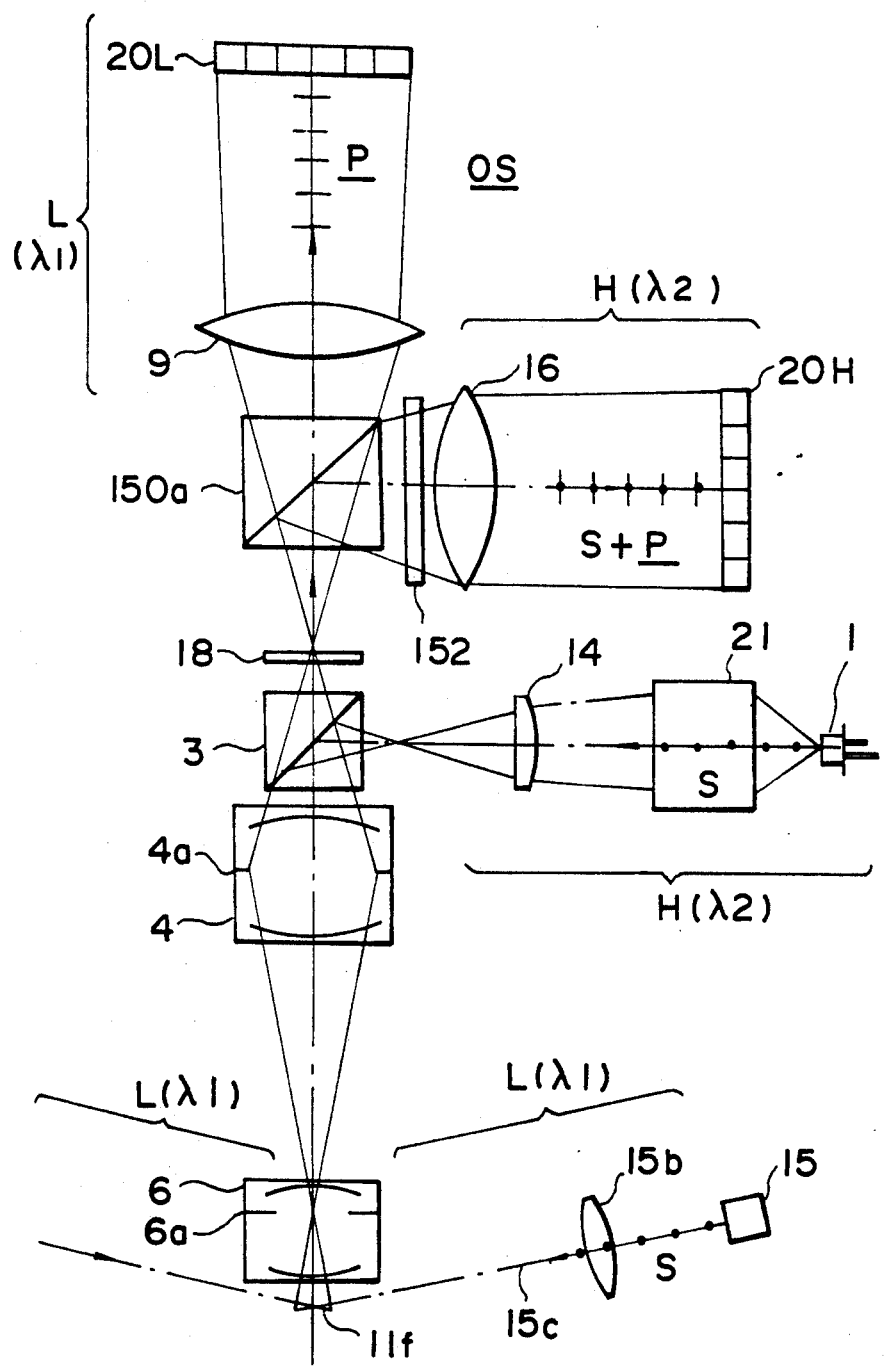

FIGS. 4 through 6 are optical path diagrams of the polarization states, which illustrate three examples of polarizations in the optical system in FIG. 1. In FIG. 4 through FIG. 6, both the oblique illumination system L and the vertical illumination system H perform S polarization (i.e., linear polarization having oscillation components in the X direction). The scattered light 12 from the pattern 2 and foreign substance 13 on the surface of the sample 7 is a mixture of P-polarized light (i.e., linear polarization having oscillation components in the Y direction) and S-polarized light. The wavelengths of the illumination beams 15c,11 of the illumination systems L, H are $\lambda_1$ or $\lambda_2$, and are different from each other. The scattered light 12 from the respective illumination systems L,H is separated by the color-separation prism 150 and reach the corresponding detectors 20L,20H. In the exemplary polarization shown in FIG. 4, both polarized lights (S+P) of the scattered light 12 are detected by each of the detection systems L,H. This polarization permits a faster inspection compared to the second example of the prior art. In the illustrative polarization depicted in FIG. 5, P-polarized light is detected by providing the detection system with a deflector element 151 such as an analyser. Compared to the second example of the prior art, the polarization of FIG. 5 makes it possible to improve the discrimination ratio of the foreign substance 13 to the pattern 2. The polarization depicted by way of example in FIG. 6 makes use of a dichroic prism 150a having color separation and polarization characteristics. Owing to its combined use with a color filter 152, color separation is feasible. The polarization of this example can also bring about an improved discrimination ratio.

Figure 7A:
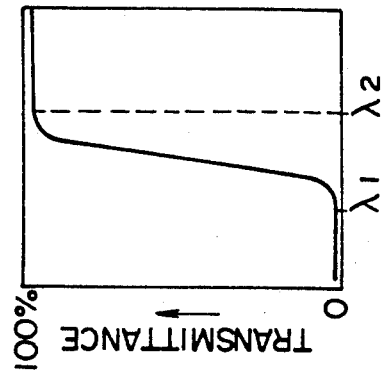
FIG. 7A through FIG. 7C are transmission characteristic diagrams of optical elements in FIG. 5 and FIG. 6.
Figure 7B:
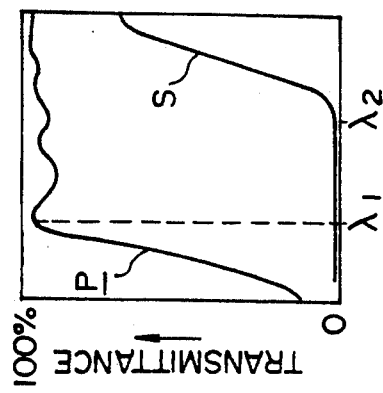
Figure 7C:
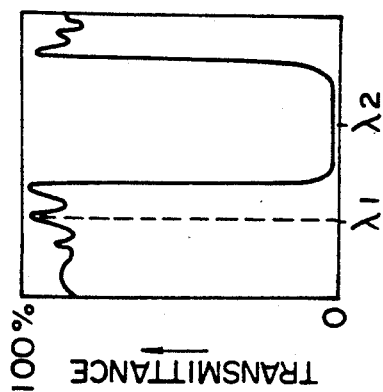

FIGS. 7A through 7C are transmission characteristic diagrams of the color-separation prism 150, dichroic prism 150a and color filter 152 shown in FIGS. 4 through 6, respectively. FIGS. 7A through 7C show transmittances T (%) of the color-separation prism 150, dichroic prism 150a and color filter 152 for wavelengths including the wavelengths $\lambda_1,\lambda_2$ of the illumination beams in the illumination systems L,H. Incidentally, various means such as a combination of a semitransparent mirror (or semitransparent prism) and a color filter can be contemplated for color separation.

Figure 8:
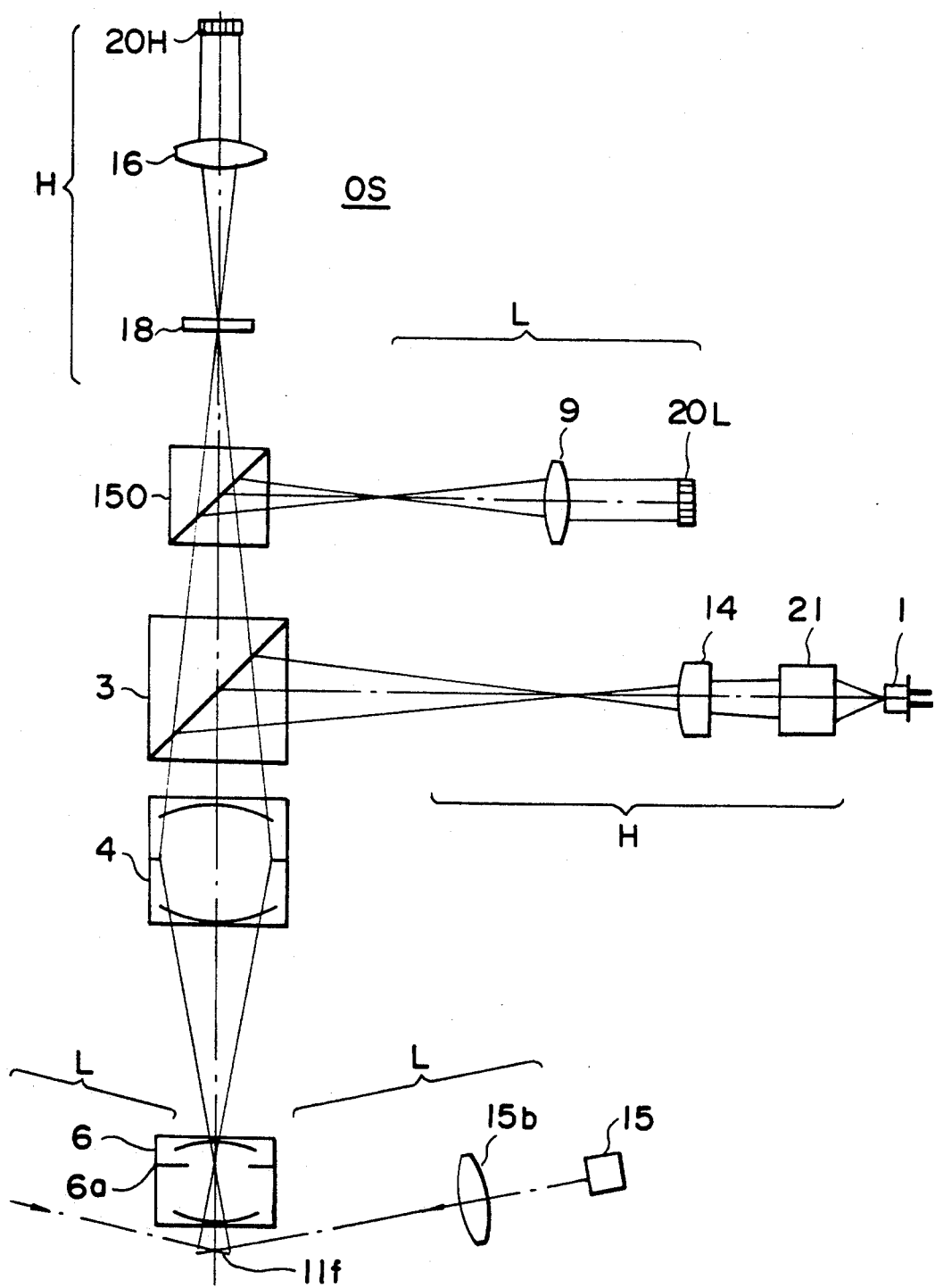
FIG. 8 is an optical path diagram of another optical system, showing a second embodiment of the present invention.

FIG. 8 is an optical path diagram of illumination and detection systems which illustrates a second embodiment of the method and apparatus of this invention for the detection of foreign substances on a patterned wafer. While the light shutoff plate 18 is arranged on the lower side of the color-separation prism 150 in FIG. 1 through FIG. 6, the light shutoff plate 18 is disposed on the upper side of the color-separation prism 150 in the embodiment of FIG. 8. This arrangement allows the detection system L to achieve effective detection of the scattered light 12 from the foreign substance 13 as a result of illumination by the oblique illumination system L without being affected by the light shutoff plate 18.

Figure 9A:
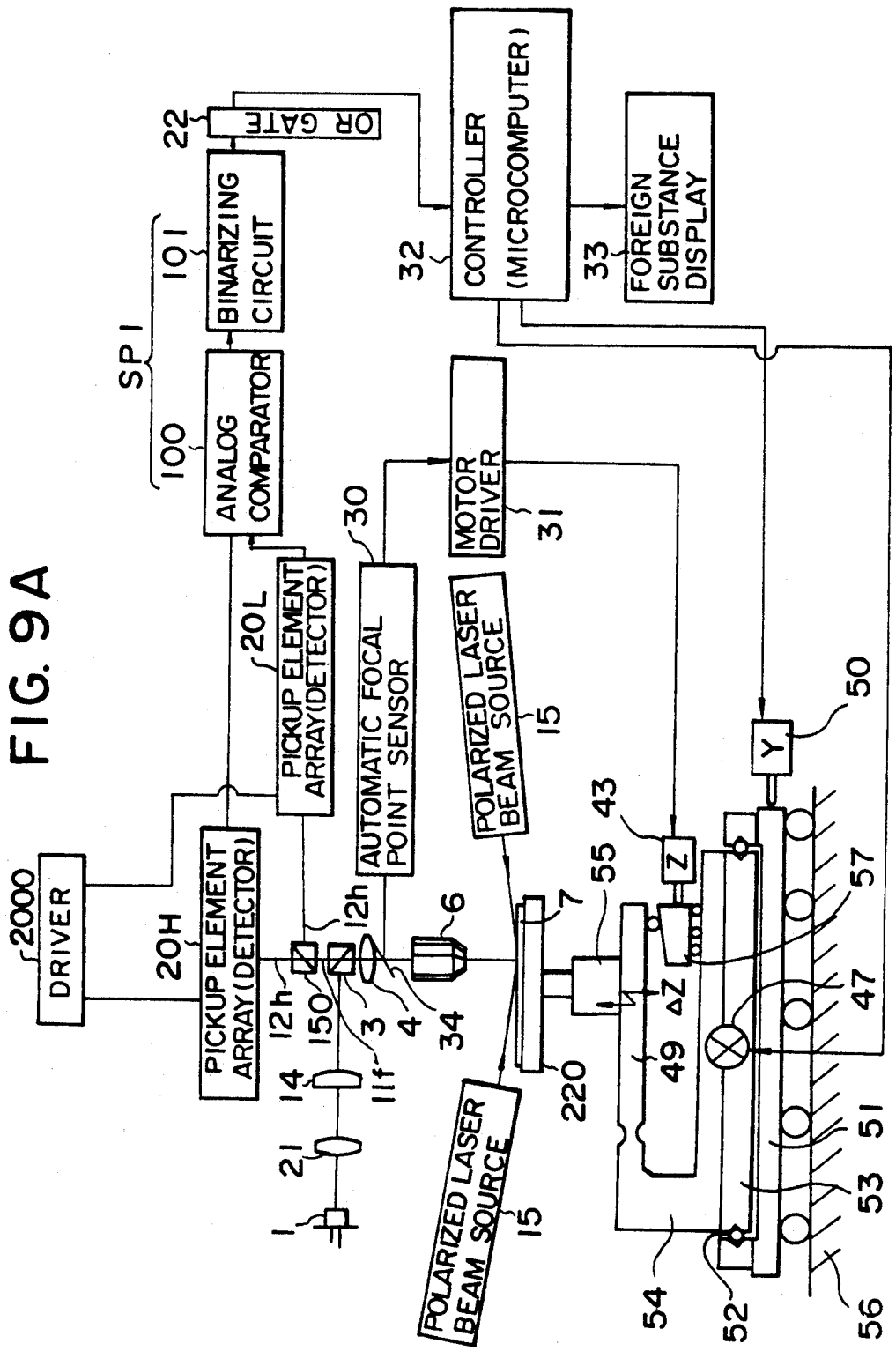
FIG. 9A is a block diagram of one example of an apparatus useful in the present invention.
Figure 9B:
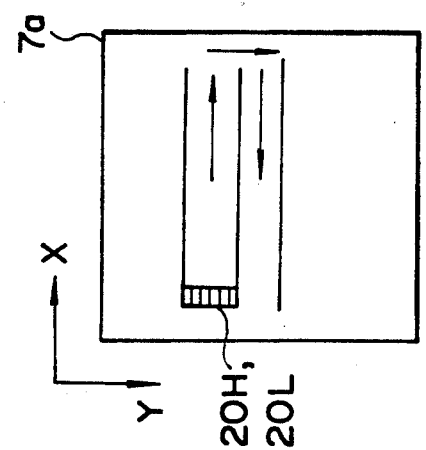
FIG. 9B and FIG. 9C schematically illustrate exemplary feeding methods for a sample, respectively.
Figure 9C:
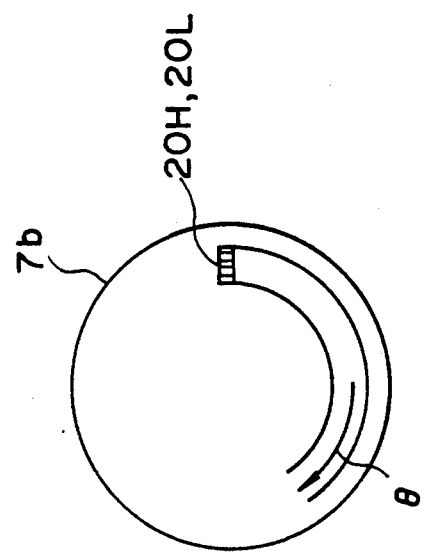

FIG. 9A and FIGS. 9B and 9C are a block diagram showing the construction of one example of an apparatus employed in the method of the present invention for the detection of foreign substances on a patterned wafer and schematic illustrations of methods for feeding the sample, respectively. In addition to elements similar to those employed in the above-described apparatus of FIG. 1, the apparatus of this embodiment include a support and drive mechanism for supporting an object and moving the object along the X axis, the Y axis and the Z-axis, an automatic focus control means for performing the focal matching of the optical system, and a control system for controlling the operation of inspection of foreign substances on the object and outputting and processing the results of the inspection.

The support and drive mechanism comprises a feed stage 220 for supporting the object 7, a leaf spring 49 supporting the feed stage 220, a feed motor 50, a Y-axis skid 51 displaceable by the feed motor 50 on a level block, an X-axis skid 53 mounted on the skid 51 displaceably along X-axis with bearings 52 interposed therebetween, another feed motor 47 for driving and displacing the X-axis skid 53, a support table 54 mounted on the X-axis skid 53 and supporting the leaf spring 49, a Z-axis drive motor 43 actuated responsive to a command from the automatic focus control means to either lift or lower the stage 220, a Z-axis drive mechanism 57 for lifting or lowering the stage 220 upon transmission of a torque from the motor 43, and a stage-turning mechanism 55 having a function to turn the stage 220. The stage-turning mechanism 55 is required only when the detection of foreign substances is performed by turning the object. Otherwise, the stage-turning mechanism 55 can be omitted.

The automatic focus control means has an automatic focusing sensor 30 constructed of plural photoelectric elements, an electric circuit for actuating the photoelectric elements and obtaining outputs from the photoelectric elements and an arithmetic circuit for detecting a focal-point matching position, said photoelectric elements, electric circuit and arithmetic circuit being all free of illustration; and a motor driver 31 for driving and controlling the Z-axis drive motor 43 to perform focal-point matching on the basis of an output from the automatic focusing sensor 30.

The control system comprises a controller 32 formed, for example, of a microcomputer, and a foreign substance display 33 for displaying foreign substances on the basis of display output signals from the controller 32.

The controller 32 is composed, for example, of a central processing unit, a memory, an input/output interface, etc., all not shown. The controller 32 performs the processing of a foreign-substance detection signal outputted from the OR gate 22, the control of movement of the stage 220 in the X-Y direction (i.e., the control of scanning of the object), the control of rotation of the object when the object is rotated, the control of the entire apparatus, etc.

In the drawing, numeral 2000 indicates a driver for driving and controlling the detectors (solid pickup element arrays) 20L,20H.

Figure 27:
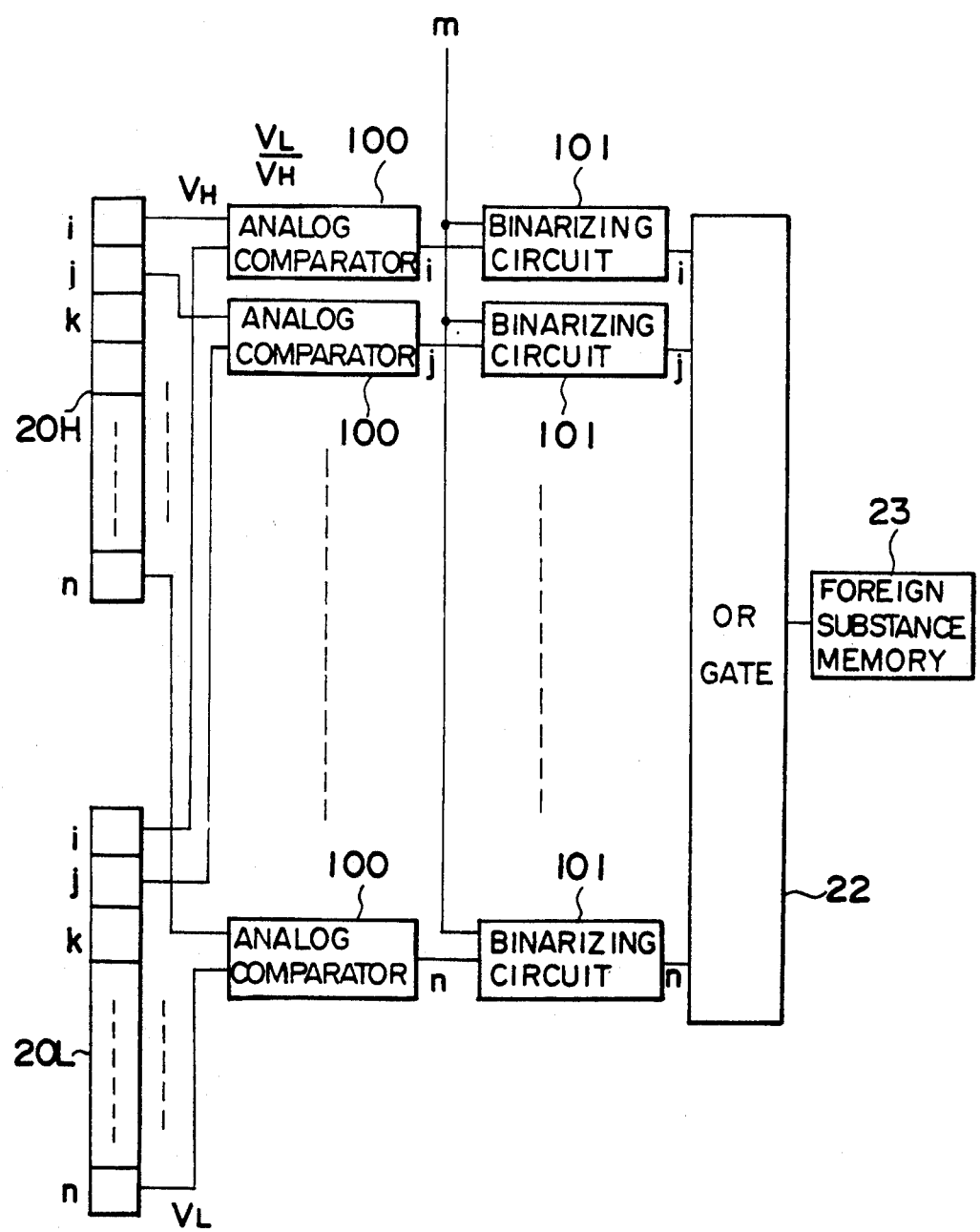
FIG. 27 is a detailed circuit diagram of the signal processing circuit of FIG. 23.

In FIGS. 9A through 9C, the detection sensitivity can be improved over the second example of the prior art when the ratio $V_L/V_H$ of the output signals $V_L,V_H$ from the solid pickup element arrays 20L,20H in FIG. 9A is computed by the analog division comparator 100 (as illustrated in FIG. 17i) and is then converted to a binary signal with respect to the threshold value m by the binarizing circuit 101 (as shown in FIG. 17j). In this case, it is necessary to use plural analog division comparators 100 and plural binarizing circuit 101 for the pixels i-n of the solid pickup element arrays (detectors) 20L,20H, whereby analog division comparisons can be performed concurrently (see FIG. 27). The OR gate 22 outputs a foreign substance signal (i.e., "1" in FIG. 17j), which has been produced at any one of the pixels i-n of the detectors 20L,20H, to the foreign substance display 33. The one-dimensional solid pickup element arrays (detectors) 20L,20H are provided at the imaging position 12h of the linear laser spot 11f. These arrays are subjected to simultaneous scanning, i.e., are scanned in the Y-direction by the common driver 2000. Further, by combining X-axis feeding of the feed stage 220 with the sample 7 carried thereon, the sample 7 can be scanned two-dimensionally. When the sample 7a is rectangular as shown FIG. 9B, the sample 7a is fed in a zig-zag pattern in the X-Y direction. When the sample 7b is circular as illustrated in FIG. 9C, the length of the linear laser spot 11f is aligned with a radius of the sample 7b and the sample 7b is spirally fed in the direction θ.

A description will next be made of the third embodiment of the method and apparatus of this invention for the detection of foreign substances, which embodiment is suitable for the detection of foreign substances on a mirror-finished surface such as a surface of a polished semiconductor wafer.

Figure 10:
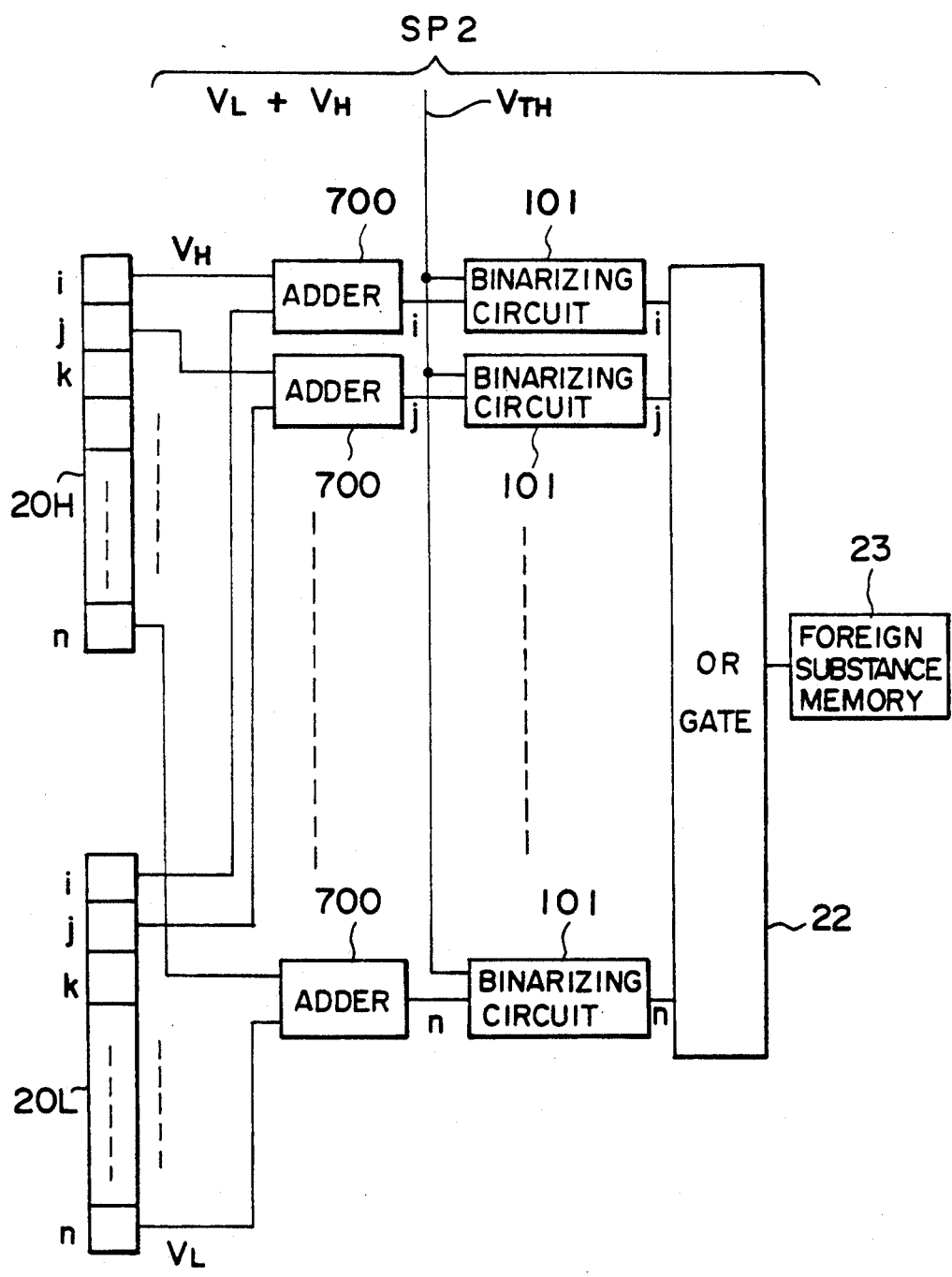
FIG. 10 is a block diagram of a signal processing circuit useful in a third embodiment of the present invention.

This embodiment is constructed by connecting a signal processing circuit SP2 to the optical system depicted in FIGS. 1 through 8. FIG. 10 is a block diagram of one example of the signal processing circuit.

The signal processing circuit SP2 shown in FIG. 10 has the detectors 20L,20H, adders 700, the binarizing circuits 101, the OR gate 22, and the foreign substance memory 23. Each of the detectors 20L,20H has the pixels i-n. Outputs from the individual pixels of the detectors 20L,20H are inputted in pairs, like (i,i), (j,j), . . . (n,n), to the corresponding adders 700i, . . . 700n and are added there. The output from each adder 700 is inputted to the corresponding binarizing circuit 101. The output from each binarizing circuit 101 is then delivered to the foreign substance memory 23 by way of the OR gate 22.

The reflected light 11 from the sample 7 in the optical system of FIGS. 1 through 8 is completely shut off by the light shutoff plate 18, whereas the reflected light 12 is allowed to reach the detectors 20L,20H in its entirety. The output signals $V_L$, $V_H$ from the detectors 20L,20H are inputted to the adder 700, so that the signal $V_L$ and the signal $V_H$ are added together to obtain a signal $V_L+V_H$. The resultant signal is converted to a binary signal with respect to a threshold value $V_{TH}$ at the binarizing circuit 101, whereby a foreign substance signal is obtained. The sensitivity for the detection of foreign substances has been improved in this embodiment compared to the second example of the prior art, because scattered light 12 from the foreign substance 13 as a result of the oblique illumination L and the vertical illumination H can be effectively detected and the light reflected from the surface of the sample can be completely shut off.

Figure 11:
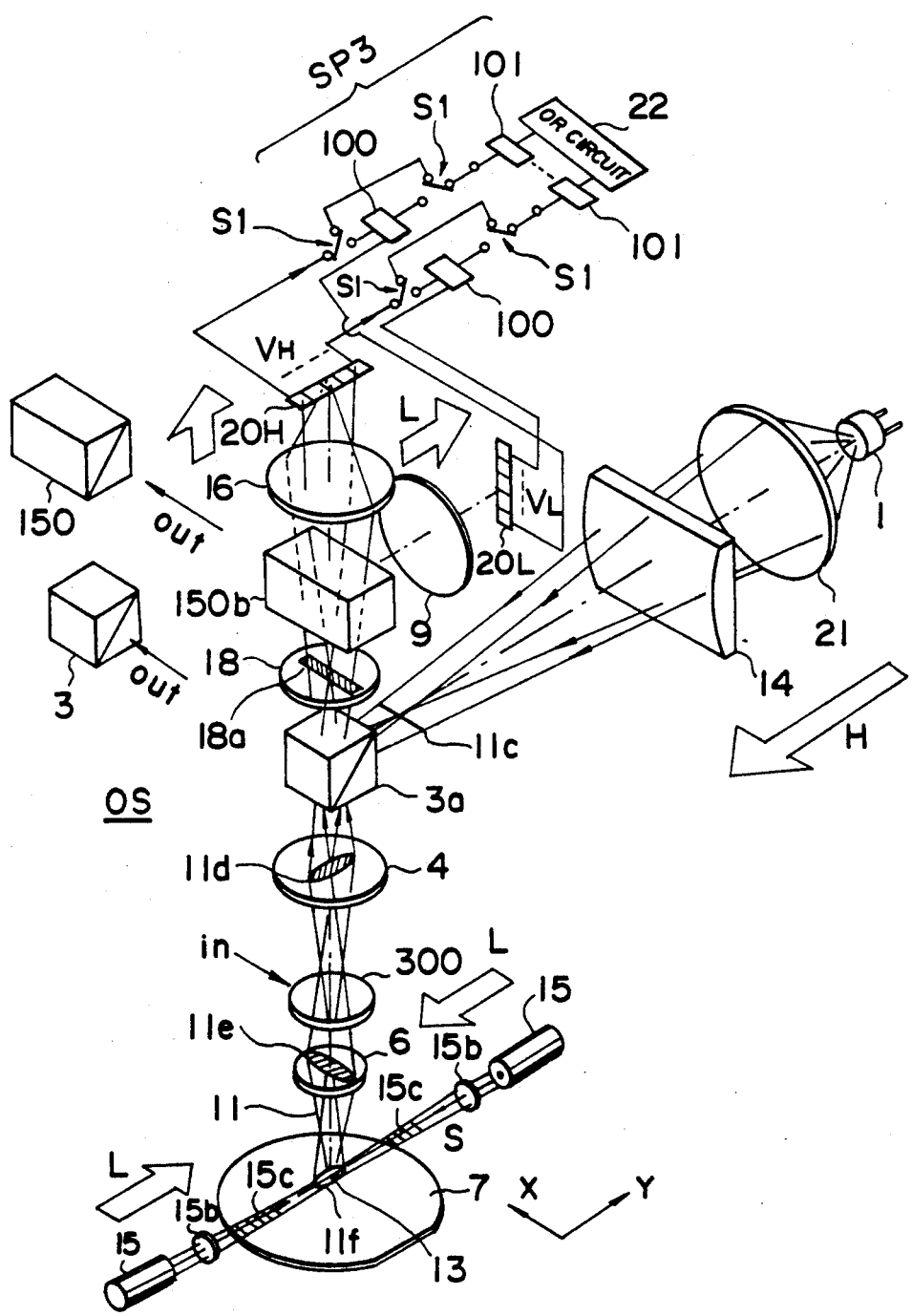
FIG. 11 is a perspective view of an optical system, illustrating a fourth embodiment of the present invention.
Figure 12:
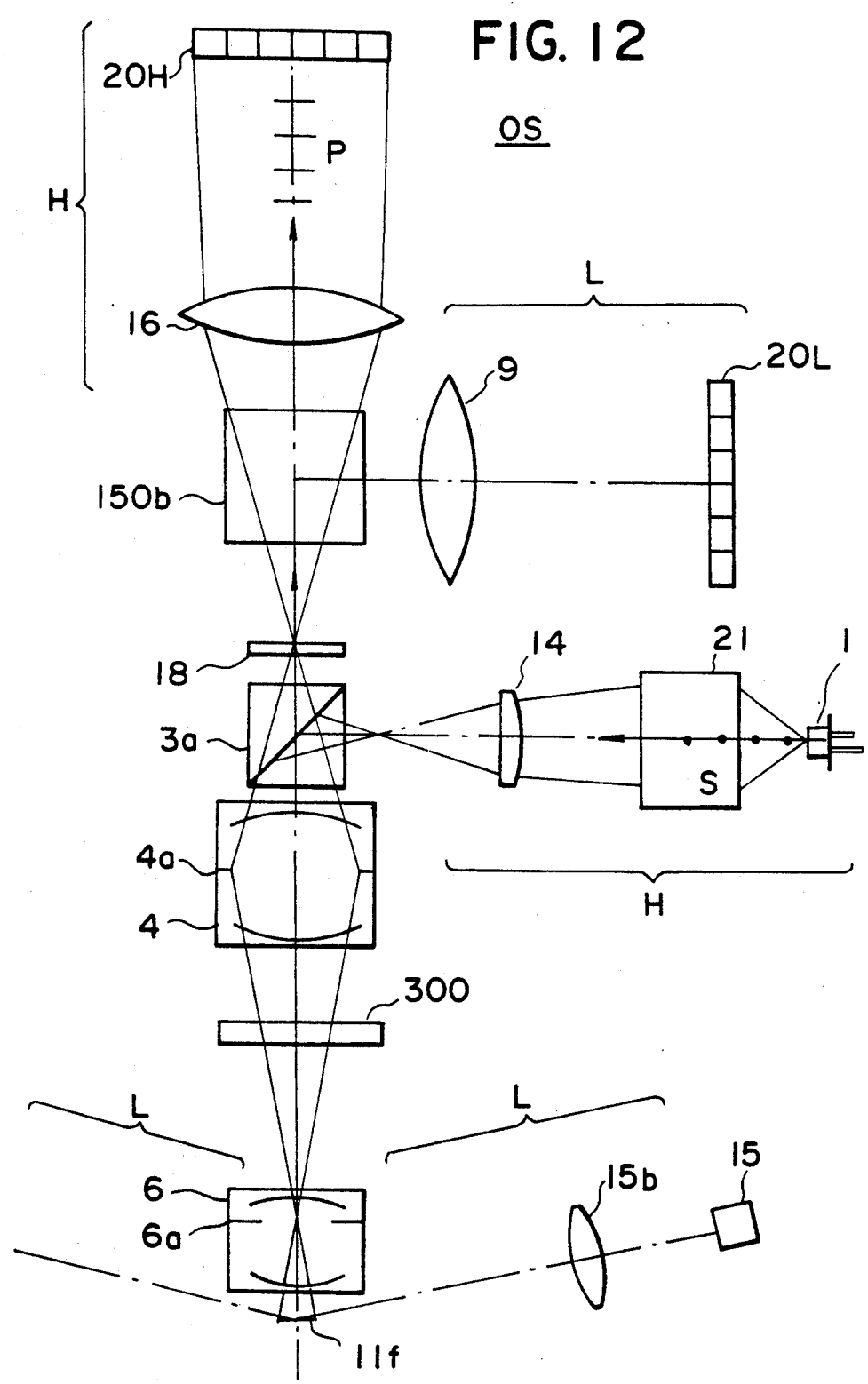
FIG. 12 is an optical path diagram of polarization in FIG. 11.

FIG. 11 is a perspective view of illumination and detection systems, illustrating the fourth embodiment of the method and apparatus of the present invention for the detection of foreign substances. The fourth embodiment is suitable for the detection of foreign substances on a mirror-finished surface. FIG. 12 is an optical path diagram of the state of polarization depicted in FIG. 11.

In the fourth embodiment, the intensity of light scattered from a foreign substance as a result of illumination by the vertical illumination H is increased further compared to the corresponding intensity in the embodiment of FIG. 10 in view of the fact that strong light is scattered from the foreign substance by the vertical illumination H. In the construction of this embodiment, the elements which are different from those of the optical system of FIGS. 1–8 are a polarization beam splitter or polarizing prism 3a and a glass block 150b. The glass block 150b serves to correct the length of the optical path. These optical elements are inserted and arranged in the optical path by a change-over mechanism, which is indicated by arrows IN,OUT in the drawing. The oblique illumination L is not used in this case.

In the signal processing means SP3 of the embodiment shown in FIG. 11, the analog comparators 100 can be bypassed by their corresponding switches S1. These switches S1 are changed over in association with the change-over mechanism for the optical elements. Since the oblique illumination system L is not used in the state of the optical system OS shown in FIG. 11, each switch S1 is changed over to deliver an output from the detector 20H to the associated binarizing circuit 101 by bypassing the corresponding analog comparator 100.

When the oblique illumination system L is employed, the switches S1 are changed over into a state different from that depicted in FIG. 11 so that the embodiment is allowed to function, for example, in the same manner as the embodiment shown in FIG. 1.

The apparatus of this embodiment therefore enables the operation mode to be selected in view of the surface condition of an object so that it takes the state of FIG. 1 upon detection of foreign substances on a patterned object such as a semiconductor wafer or the state of FIG. 11 upon detection of foreign substances on a mirror-finished surface. It is hence possible to perform both the detection of foreign substances on a patterned object and the detection of foreign substances on a mirror-finished surface by changing over the switches of the single apparatus.

In the above construction, the laser beam 11 emitted from the laser beam source 1 is S-polarized light. After passing through a polarizing prism 3a, the S-polarized light forms the laser beam spot 11d in the diaphragm 4a of the field lens 4. Subsequent to passage through the field lens 4, the laser beam 11 travels through a quarter wave plate 300 and, by the object lens 6, forms the laser beam spot 11f on the sample 7. When the foreign substance 13 does not exist on the sample 7, the reflected laser beam (zeroth-order diffracted light) 11 from the surface of the sample 7 again passes through the object lens 6, quarter wave plate and field lens 4. After being transmitted 100% through the polarizing prism 3a, the reflected laser beam is shut off by the light shutoff portion 18a of the shutoff plate 18. The field lens 4 forms and projects, on the light shutoff portion 18a, the image of the spread 11e of the laser beam in the diaphragm 6a of the object lens 6. The light shutoff plate 18 can be obtained, for example, by centrally forming the light shutoff portion 18a with an opaque film on a transparent glass. When the illumination laser 11 passes through the quarter wave plate 300, the S-polarized light of the illumination beam 11 is changed to the P-polarized light of the reflected light 11. Therefore, the reflected light 11 is allowed to transmit 100% through the polarizing prism 3a.

When there is the foreign substance 13 on the sample 7, exposure of the foreign substance 13 to the illumination beam 11 results in the generation of scattered light (higher-order diffracted light) 12 from the foreign substance 13, for example, as will be described with reference to FIG. 14B(a). The scattered light 12 spreads all over the area in the diaphragm 6a of the object lens 6 and returns along the same optical path as the reflected light 11. Since the foreign substance 13 has minute ruggedness, the scattered light 12 is depolarized and contains both S-polarized light and P-polarized light. P-polarized light is however paramount after the scattered light 12 has passed through the quarter wave plate 300. After transmission through the polarizing prism 3a, this P-polarized light passes through the transmitting portion of the light shutoff plate 18, said transmitting portion being located outside the light shutoff portion 18a, and is condensed by the imaging lens 16 and eventually reaches the detector 20H. According to this embodiment, the intensity of the light scattered from the foreign substance was as high as at least 4-fold the intensity available with the apparatus of the embodiment of FIG. 10 owing to the replacement of the semitransparent prism 3 by the polarization beam splitter 3a.

A description will next be made of a fifth embodiment of the present invention. The apparatus according to the fifth embodiment has an optical system of the same construction as that illustrated in FIG. 11 (FIG. 12) except that the color-separation prism 150 is used and the signal processing circuit of FIG. 10 is also employed. According to this embodiment, the advantages of the embodiment of FIG. 10 and those of the embodiment of FIG. 11 are both obtained. In this embodiment, the scattered light 12 from the foreign substance 13 as a result of illumination by the oblique illumination L is partly reflected and lost when it passes through the polarization beam splitter 3a subsequent to the passes through the quarter wave plate 300. The scattered light 12 from the foreign substance 13 as a result of illumination by the vertical illumination H is the same as in the embodiment of FIG. 11 (FIG. 12) and the intensity of light scattered by the foreign substance 13 is increased further compared to that available by the embodiment of FIG. 11.

FIG. 13 schematically illustrates polarization characteristics of the scattered light 12 from the foreign substance 13 upon illumination by the same oblique illumination L as in the embodiment of FIGS. 1 through 12. FIG. 13(a) shows scattered lights 12(S),12(P) from the foreign substance 13 when the oblique illumination beam 15c intended to highlight the foreign substance 13 on the sample 7 is S-polarized light. FIGS. 13(b) through 13(d) show the corresponding output signals $V_L(S)$, $V_H(P)$, $V_L(P+S)$ from the detector 20L, respectively. The scattered light 12 given off from the foreign substance 13 upon illumination by the oblique illumination beam (S-polarized light) contains S-polarized scattered light 12(S) and P-polarized scattered light 12(P) as shown in FIG. 13(a). When the size of the foreign substance 13 is not greater than about 1 μm, the scattered light 12(S) whose polarization has not been changed is as large as 10-fold to 100-fold compared to the scattered light 12(P) whose polarization has been changed. The apparatus of this embodiment can therefore detect either one of output signal $V_L(S)$ and output signal $V_L(P+S)$ resulted from the scattered lights 12(S) and 12(P+S) in FIGS. 13(b) and 13(d), respectively, although the output signal $V_L(P)$ corresponding to the scattered light 12(P) in FIG. 13(c) is detected in the second example of the prior art. The intensity of the output signal $V_L$ is therefore increased compared to the second example of the prior art so that the S/N ratio of the output signal $V_L$ becomes large. This has realized high-speed inspection.

Figure 14A:
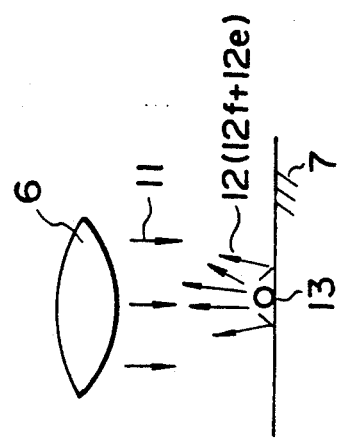
FIG. 14A through FIG. 14D show the directions of scattered light from oblique illumination and vertical illumination in FIG. 1 through FIG. 12.
Figure 14C:
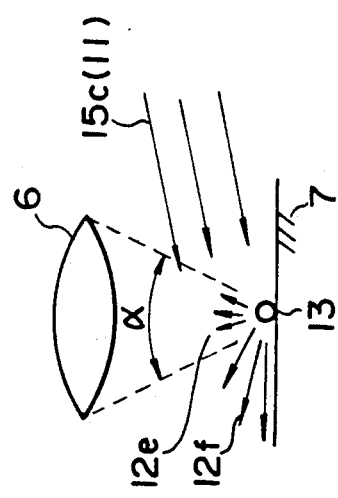
Figure 14B:
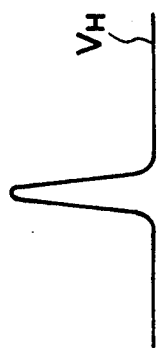
Figure 14D:
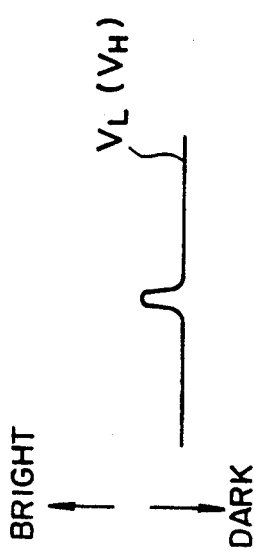

FIGS. 14A through 14D schematically show the directions of the scattered lights 12 from the foreign substance 13 upon illumination by the oblique illumination L and vertical illumination H in the embodiment of FIGS. 1 through 12. FIG. 14A shows forward scattered light 12f and side-way scattered light 12e from the substance 13 upon illumination by the oblique illumination beam 15c(11). FIG. 14B depicts the resulting signal $V_L(V_H)$. FIG. 14C illustrates scattered light 12 (12f+12e) from the substance 13 upon illumination by the vertical illumination beam 11, while FIG. 14D shows the resulting output signal $V_H$. When the substance 13 in FIG. 14A is a foreign substance of the submicron order as small as about 0.1 μm, the forward scattered light 12f is paramount in the scattered light 12 produced form the foreign substance as a result of the illumination by the oblique illumination 15c(11), and the side-way scattered light 12e impinging upon the object lens 6 is weak. It is therefore desirable to enlarge the angular aperture α of the object lens 6 so that the forward scattered light 12f can also be detected in part. Limitations are however imposed on the angular aperture. No sufficient light quantity is however obtained from the foreign substance 13 of 0.1 μm on the mirror-finished sample in this case as is illustrated in FIG. 14B, so that the output signal $V_L(V_H)$ from the detector 20L(20H) is too weak to permit its detection. When the foreign substance 13 in FIG. 14C is a foreign substance of the submicron order as small as about 0.1 μm, the scattered light 12 (12f+12e) produced upon illumination by the vertical illumination beam 11 can be effectively condensed by the object lens 6, thereby making it possible to detect the same. As a result, the output signal $V_H$ from the detector 20H becomes large as shown in FIG. 14D. Owing to the use of the vertical illumination H in this embodiment, the high-sensitivity detection of the fine foreign substance 13 on the mirror-finished surface and the detection of the fine foreign substance 13 on the pattern 2 can be realized by the same optical system.

Figure 15A:
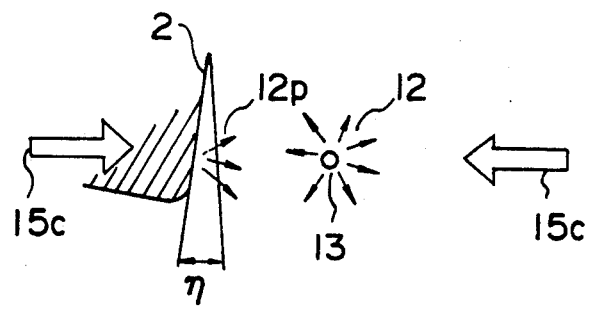
FIG. 15A through FIG. 15C schematically illustrate the results of experiments under the illumination and analysis conditions in FIG. 1 through FIG. 12.
Figure 15B:
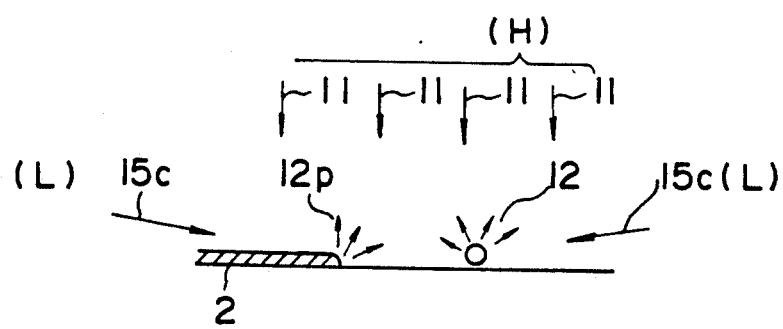
Figure 15C:
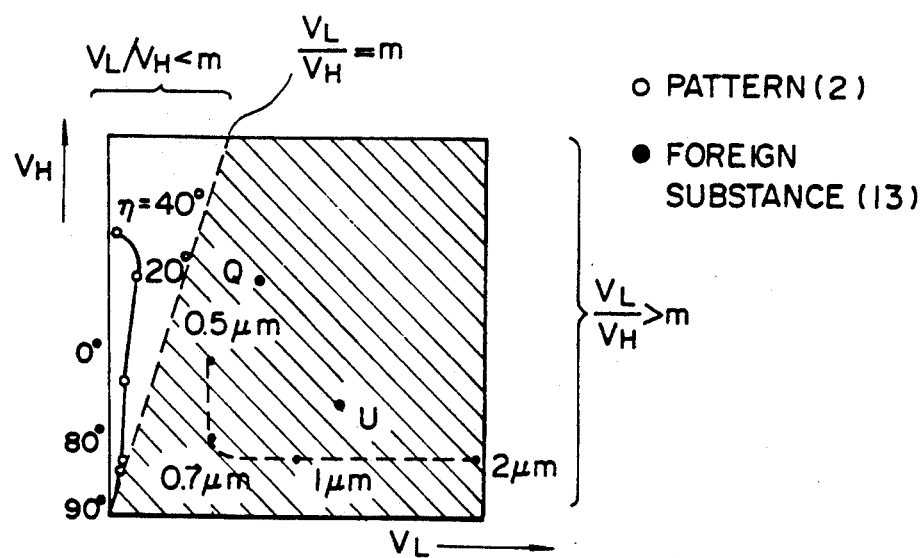
Figure 28A:
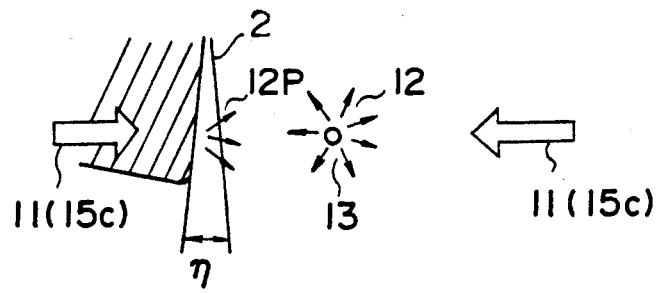
FIG. 28A through FIG. 28C schematically depict the results of an experiment under the illumination and detection conditions of FIG. 23.
Figure 28B:
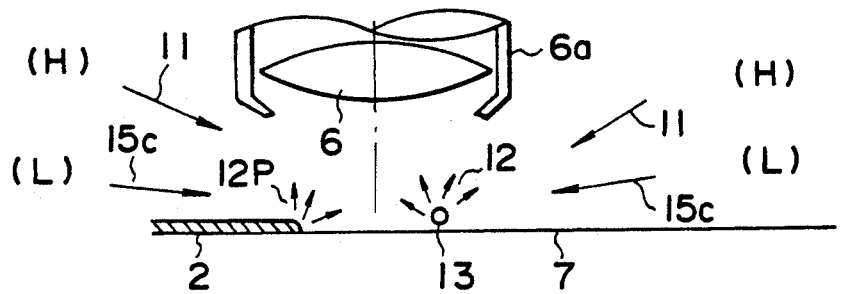
Figure 28C:
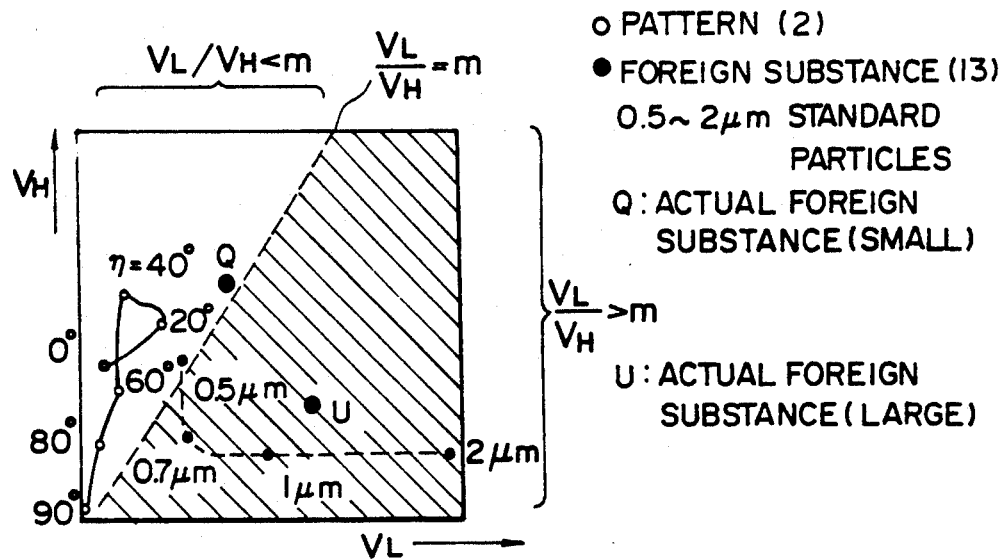
Figure 29A:
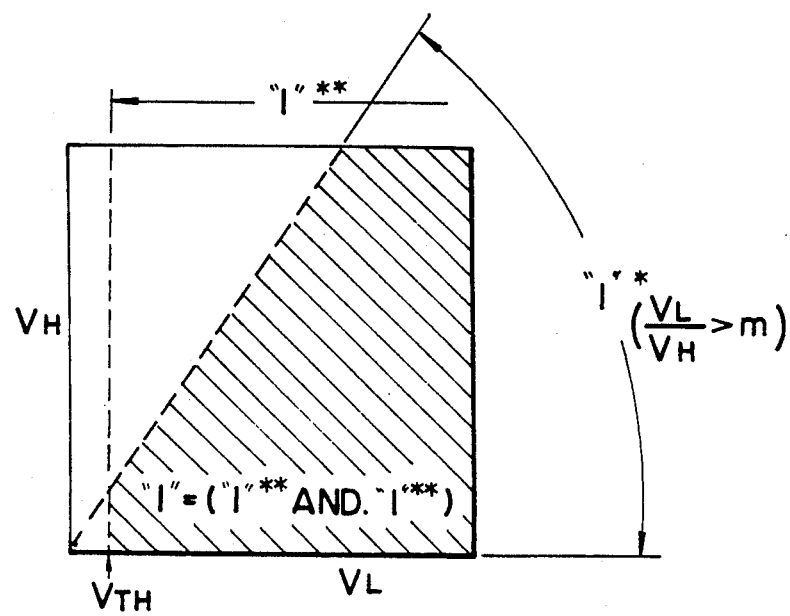
FIG. 29A is a characteristic diagram of the output signal ratios of FIG. 28C.
Figure 29B:
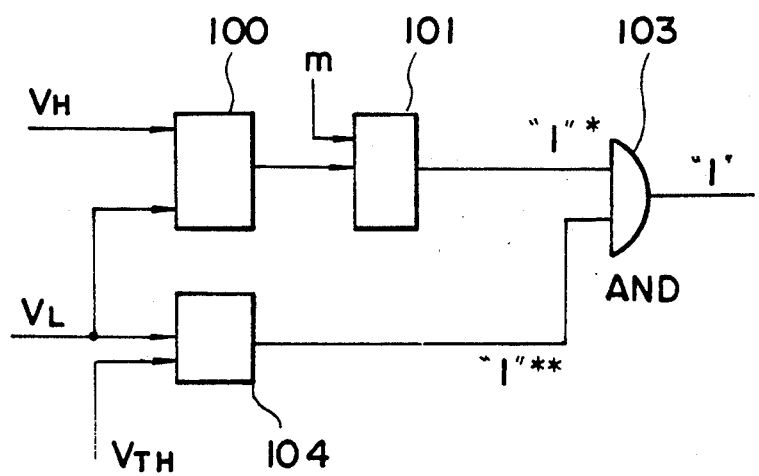
FIG. 29B is a circuit diagram of an analog division comparator for realizing the characteristics of FIG. 29A.
Figure 30A:
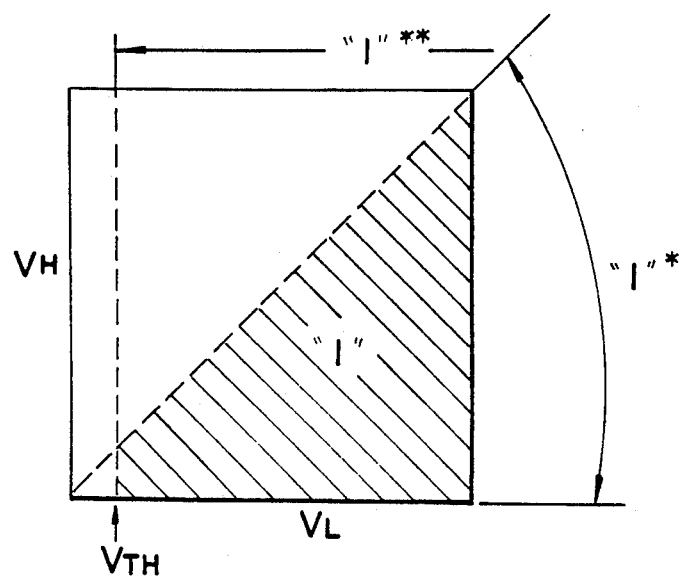
FIG. 30A is a characteristic diagram of the output signal differences in FIG. 28C.
Figure 30B:
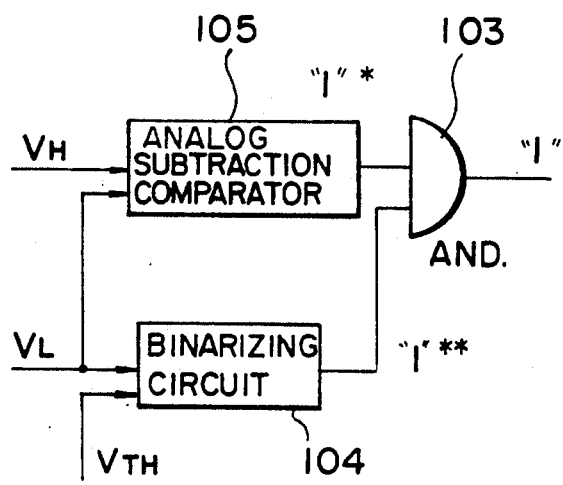
FIG. 30B is a circuit diagram of an analog subtraction comparator for realizing the characteristics of FIG. 30A.

FIGS. 15A through 15C schematically illustrate the results of an experiment under the illumination and analysis conditions of the embodiment shown in FIGS. 1 through 12. FIG. 15A and FIG. 15B are plan view and side view of the states of the scattered lights 12p12 from the circuit pattern 2 and the foreign substance 13 on the sample 7 upon illumination of the illumination beams 15c,11. FIG. 15C is a diagram of the output signal $V_H$ vs, the output signal $V_L$ as obtained in the experiment. FIGS. 15A through 15C are different from the second example of the prior art shown in FIGS. 28A and 28B in that the high oblique-angle illumination H has been replaced by the vertical illumination H. In this case, as will be described later with reference to FIGS. 16A through 16E and FIG. 17, the measurement data (indicated by circles in FIG. 15C) of the output signals $V_L$, $V_H$ from the pattern 2 are different from the corresponding measurement values in FIG. 28C. From the above experimental results, it is possible to set the inclination of the discrimination threshold line m at a large value (in other words, to set the threshold value m at a small value). Measurement values (indicated by dots) of the 0.5 μm standard foreign substance particle 13 and the actual foreign substance Q of the submicron order can therefore be detected. Reasons for this advantage will next be described with reference to FIGS. 16A through 16E and FIG. 17.

FIG. 16A shows the intensity ratios of scattered lights (P-polarized lights) 12 to scattered light (P-polarized light) 12p obtained as a result of elimination of the polarization of the oblique illumination beam (S-polarized light) 15c by the foreign substances 13a, 13b, 13c and the pattern 2. FIG. 16B shows the intensity ratios of scattered lights 12 from the foreign substances 13a, 13b, 13c to scattered light 12p from the pattern 2, depending on the oblique angle φ. FIG. 16C illustrates the intensity ratios of scattered lights 12 from the foreign substances 13a, 13b, 13c to scattered light 12p from the pattern 2 when the vertical illumination beam 11 is irradiated at an angle of 90 degrees (φ=90°). FIG. 16D shows the intensity of the scattered light 12 from the fine foreign substance 13 of about 0.5 μm, the scattered light 12 from the foreign substance 13b having a height of 1 μm or greater, the scattered light 12 from the planar foreign substance 13c having minute ruggedness and the scattered light 12p from the pattern 2. In FIG. 16D, the intensity at a low oblique angle (φ=0°-5°), the intensity at a conventional oblique angle (φ=10°-30°, "H" in the second example of the prior art) and the intensity at φ=90° ("H" in the present invention) are shown in comparison to one another. Further, in the case of φ=0°-5° and φ=10°-30°, the intensity are shown separately in accordance with the causes for the scattered lights in FIGS. 16A and 16B. Incidentally, (A), (B) and (C) in FIG. 16D correspond to FIGS. 16A, 16B and 16C, respectively. Further, the words "High", "Medium" and "Low" indicate the levels of the individual intensities. FIG. 16E shows use conditions for the second example of the prior art and the embodiment of the present invention. The intensities separately shown in FIG. 16D are indicated in a totaled qualitative manner in FIGS. 17b, 17d and 17h, respectively.

Figure 17:
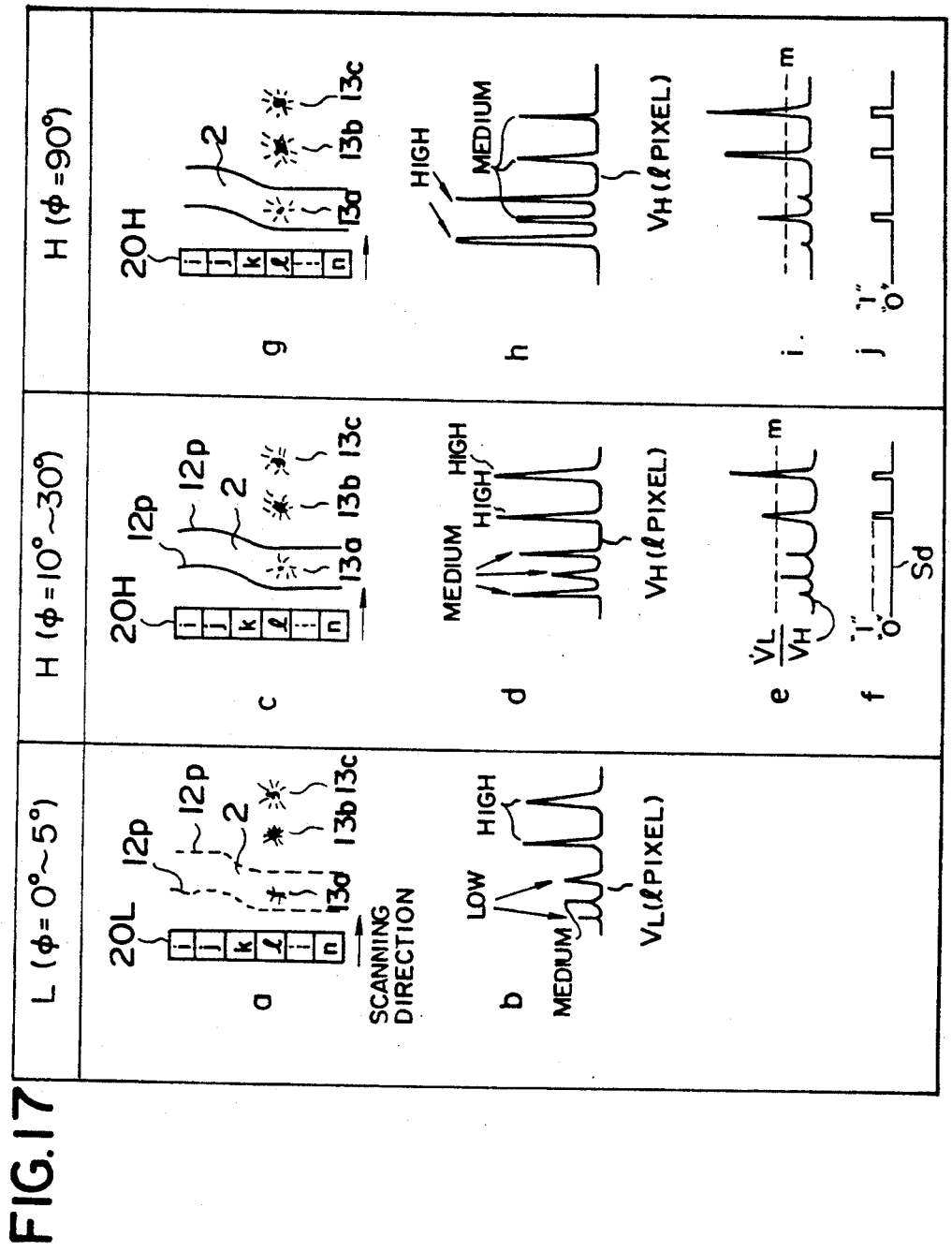
FIG. 17 schematically depicts a method for discriminating a pattern and a foreign substance from each other.
Figure 19A:
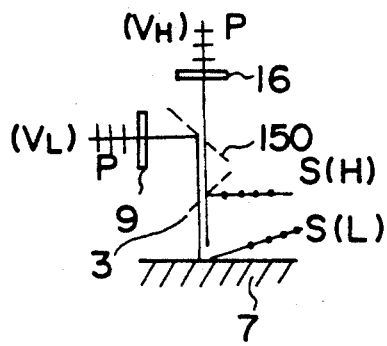
FIG. 19A through FIG. 19H and FIG. 20A through FIG. 20D are optical path diagrams of polarizations usable in the respective embodiments of the present invention.
Figure 19D:
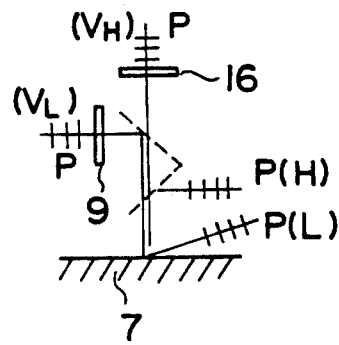
Figure 19B:
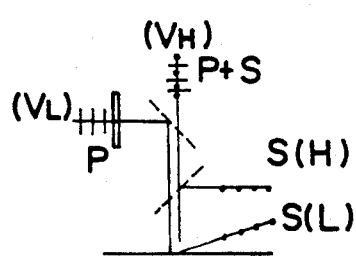
Figures 19E, 19G:
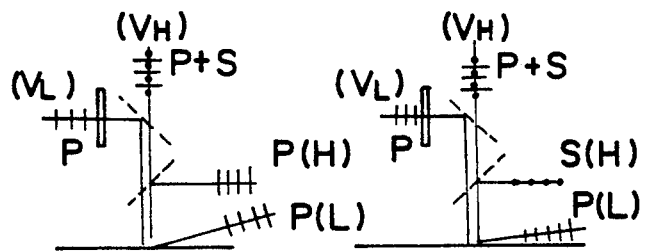
Figure 19C:
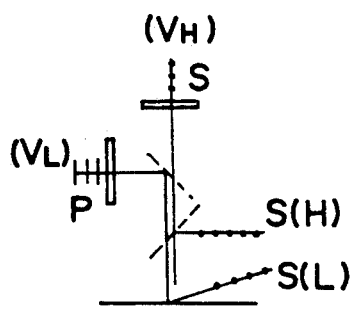
Figures 19F, 19H:
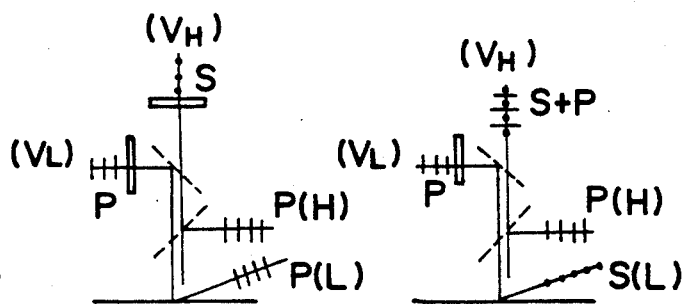
Figure 20A:
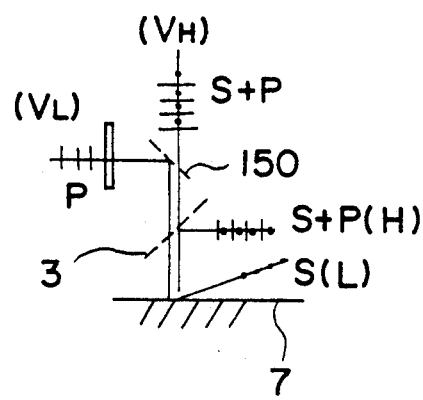
Figure 20C:
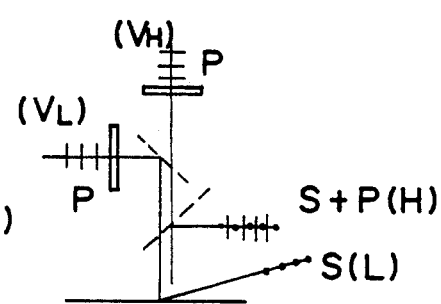
Figure 20B:
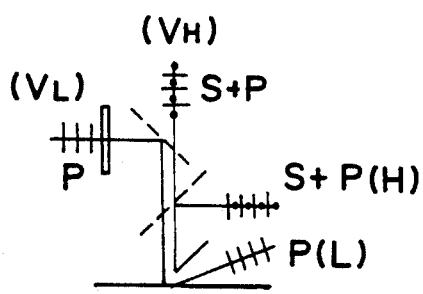
Figure 20D:
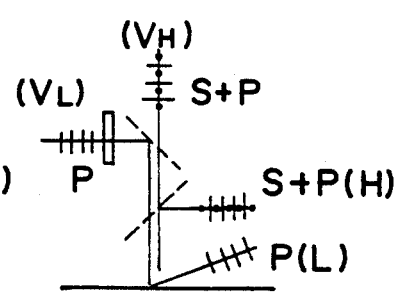
Figure 21A:
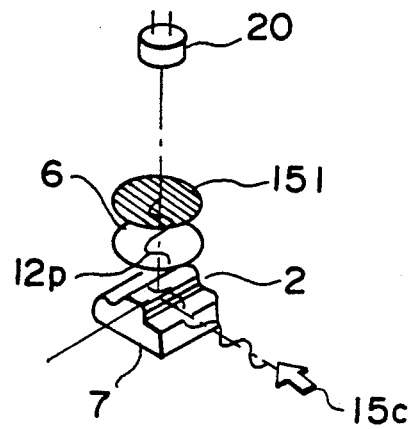
FIG. 21A through FIG 21C schematically illustrate the principle of detection by a first example of the prior art.
Figure 21B:
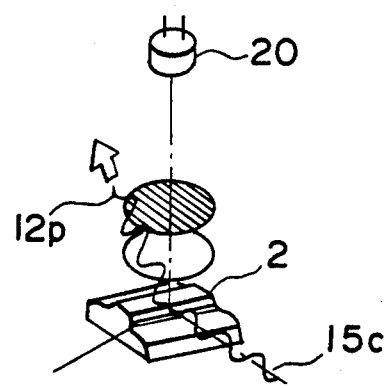
Figure 21C:
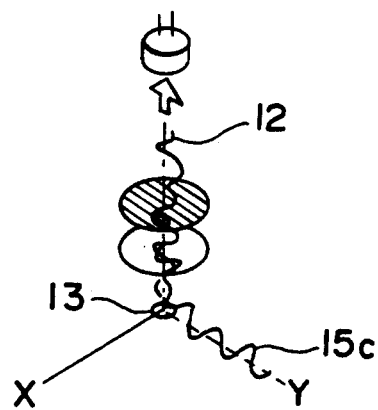
Figure 22A:
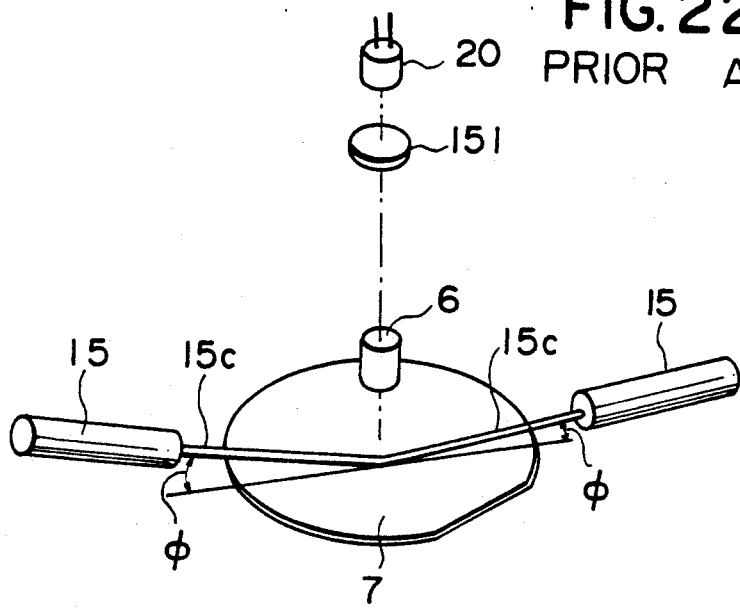
FIG. 22A and FIG. 22B are a perspective view and a discrimination ratio graph of an optical system in conventional foreign-substance-detecting method and apparatus.
Figure 22B:
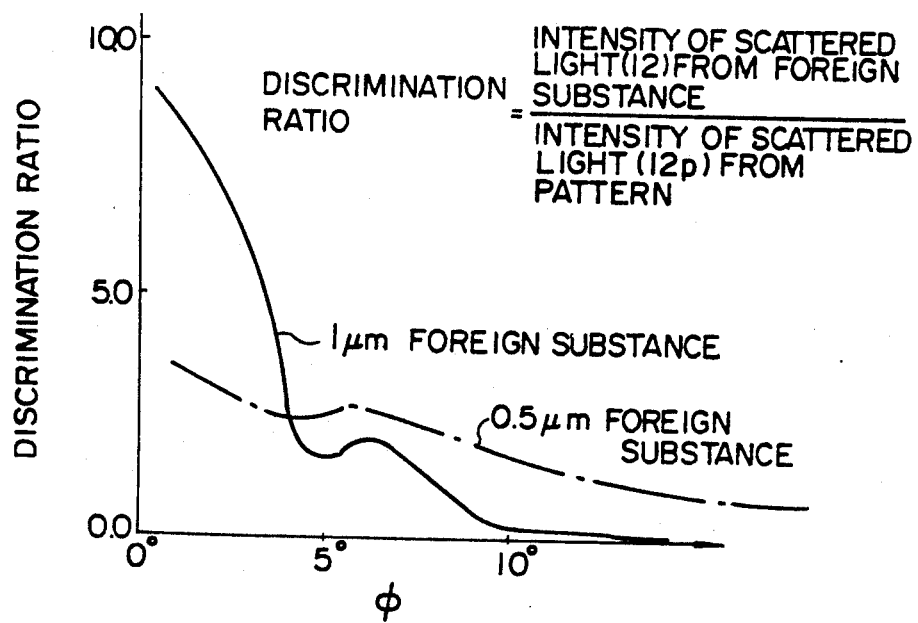
Figure 23:
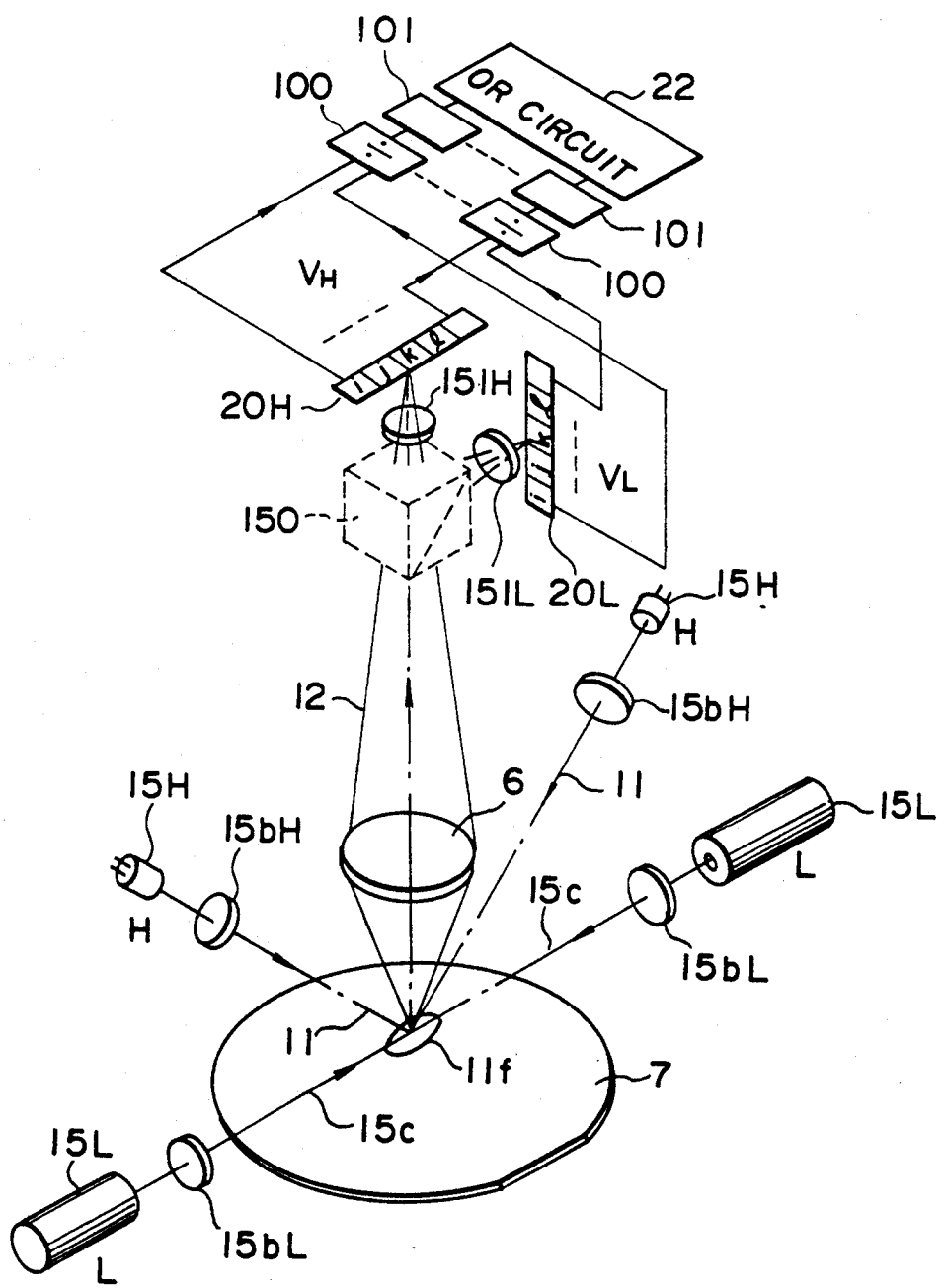
FIG. 23 is a perspective view of an optical system in a second example of the prior art.
Figures 25A, 25D:
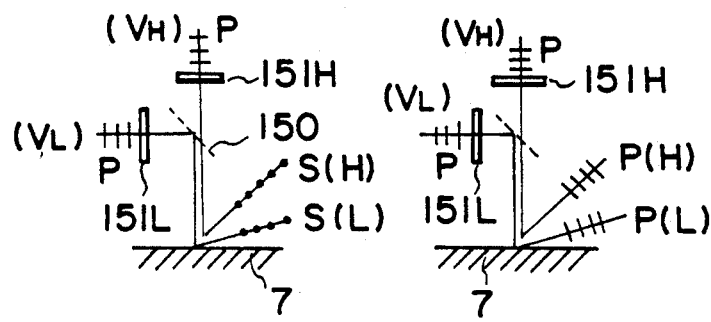
Figures 25B, 25E, 25G:
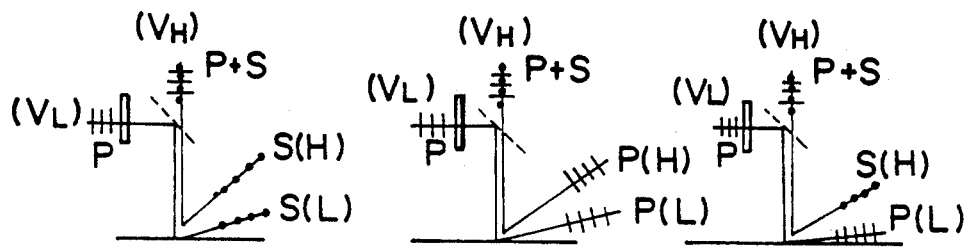
Figures 25C, 25F, 25H:
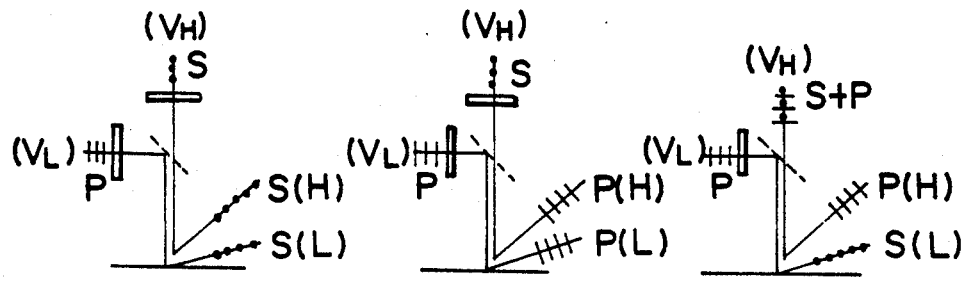

FIG. 17 diagrammatically illustrates, based on the results of FIG. 16, differences in the discrimination method for the pattern 2 and the foreign substances 13 between the second example of the prior art and the embodiment of this invention shown in FIGS. 1-12. For each of the illumination beams irradiated at L (φ=0°-5.°), H (φ=10°-30°) and H (φ=90°), the scattered lights 12p from the pattern 2 in FIGS. 17a, 17c and 17g are "small", "medium" and "high", respectively. The output signals $V_L$, $V_H$, $V_H$ in FIGS. 17b, 17d and 17h, which are outputted from the respective pixels 1 of the detectors 20L, 20H, 20HK, are "small", "medium" and "high", respectively. Accordingly, the output signal ratio $V_L/V_H$ used in the present embodiment of this invention and shown in FIG. 17i is smaller than the signal ratio $V_L/V_H$ used in the second example of the prior art and shown in FIG. 17e. The embodiment of the present invention can therefore set the discrimination threshold value m at a smaller value. Since the output signal ratio $V_L/V_H$ of the foreign substance 13a is smaller than the threshold value m in the first example of the prior art depicted in FIG. 17e, it was impossible to detect the binary signal of FIG. 17f. The present embodiment of this invention can however detect the binary signal of FIG. 17j because the output signal ratio $V_L/V_H$ of the foreign substance 13a is greater than the threshold value m in the present embodiment shown in FIG. 17i.

In the case of each of the foreign substances 13b in FIGS. 17a, 17c and 17g, the foreign substance 13b is exposed to the illumination beam 15c over a wide area of its side wall as shown in FIG. 16B because the illumination beam 15c is irradiated at the low oblique angle.

The intensity of the resulting scattered light is therefore high especially in FIGS. 17b and 17d. In the case of each of the foreign substance 13c in FIGS. 17a, 17c and 17g, the intensity of the analysis-induced scattered light is high in FIGS. 17a and 17c because of the minute ruggedness as shown in FIG. 16A, so that the output signals $V_L$, $V_H$ are high in FIGS. 17b and 17d. From the foregoing results, the output signal ratio $V_L/V_H$ of the foreign substance 13c in the present embodiment of this invention shown in FIG. 17i is greater than that of the foreign substance 13b in the second example of the prior art in FIG. 17e. The discrimination of the foreign substance 13c from the pattern 2 is therefore easier. Since the high oblique-angle illumination H in the second example of the prior art has been changed to the vertical illumination H in the embodiment of this invention, the discrimination threshold value m can be set at a smaller value so that the discrimination of the substance 13 from the pattern 2 can be facilitated. Owing to this advantage, it is not required to use the depolarization phenomenon upon illumination and detection (analysis) of the low oblique-angle illumination L when detection of foreign substances of 1 $\mu$m and greater alone is sufficient. The reasons for this feature and the advantages available therefrom have already been described with reference to FIG. 13.

FIG. 18 illustrates polarization states usable in the illumination and detection systems of each embodiment of the present invention. In FIG. 18, the polarization conditions for the illumination and detection systems of this invention are divided into the oblique illumination L (wavelength: $\lambda_1$) and the vertical illumination H (wavelength: $\lambda_2$). For each of the examples (a), (b), (c), ..., the type of polarization of each of the illuminations L,H of the illumination system and detection system is tabulated. The polarization conditions enclosed by the broken lines in the drawing indicate a range which is usable under similar polarization conditions to those employed in the second example of the prior art shown in FIGS. 25A through 26D. The range of usable polarization conditions can be broadened in the present embodiment of the invention.

The optical path diagrams of the polarization states enclosed by the broken lines in FIG. 18 are illustrated in FIGS. 19A through 20D, respectively.

FIGS. 19A through 20D are optical path diagrams of polarization states in the same range as that usable in the illumination and detection system of each embodiment of the present invention and shown in FIGS. 25A through 26D. FIGS. 19A through 20D are different from FIGS. 25A through 26D in that the S, P and S+P polarizations of the high oblique-angle illumination H, S(H), P(H) and S+P(H), have been changed to the S, P and S+P polarizations of the vertical illumination H, S(H), P(H) and S+P(H), respectively. Needless to say, detection of foreign substances not greater than 0.5 $\mu$m is feasible provided that any one of the polarization conditions in the range shown in FIGS. 19 and 20, which correspond to the polarization conditions enclosed by the broken lines in FIG. 18, is employed.

Although the above embodiments were described using a semiconductor wafer as an object, it is to be noted that the present invention is not limited to the inspection of wafers but is applicable to the inspection of other products such as photomasks and reticles.

When discrimination of foreign substances of 0.5 $\mu$m from a pattern is desired in the above embodiments, it is effective to use plural photoelectric solid pickup element arrays, in which the size of the light-receiving portion of each pixel is about 5×5 $\mu$m² when converted to the size on the sample, and to subject output signals from the individual arrays to concurrent comparison processing because the sample can be inspected with high sensitivity without deterioration of the high-speed performance.

Regarding the upper limit to the pixel size, it has already been confirmed by experiments that a pixel size as large as about 10×10 $\mu$m² does not raise any problem from the practical viewpoint when employed to detect foreign substances of 1.5-2 $\mu$m.

Although the one-dimensional solid pickup elements arrays 20L,20H were described as parallel output devices, serial output devices such as CCD (Charge-Coupled Device) can also be used.

Figure 42:
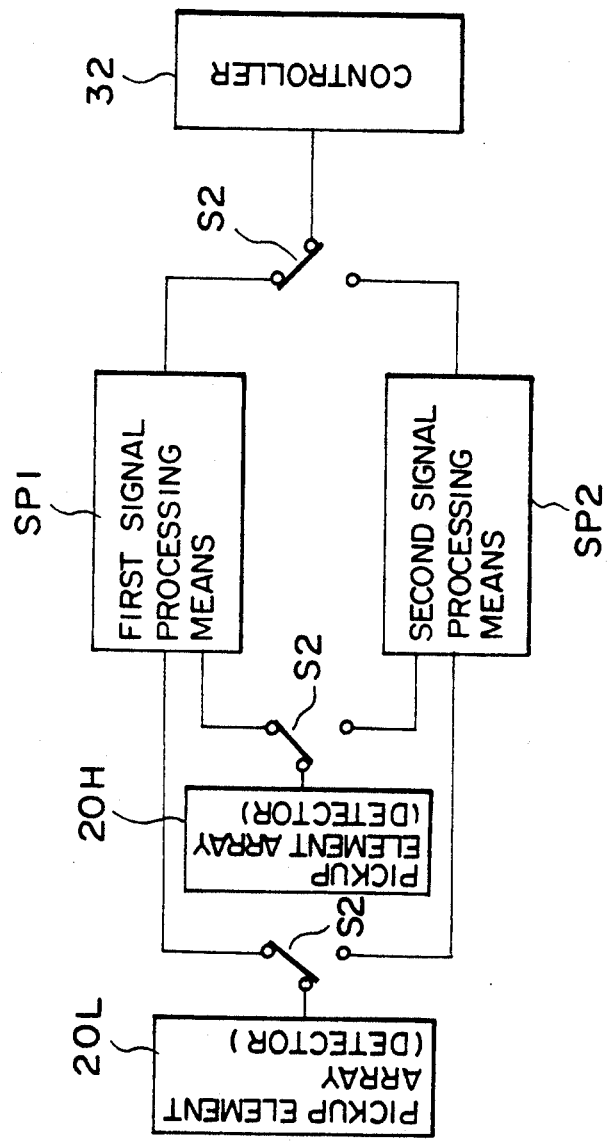
FIG. 42 is a block diagram illustrating one example of signal processing means usable in the present invention.

Further, the signal processing means useful in the present invention can also be formed as illustrated in FIG. 42, namely, by using a first signal processing means SP1 with a built-in comparator, a second signal processing means SP2 having an adder, and switches S2 connected to the input terminals and output terminals of these processing means, respectively and adapted to function as a selector means for selecting the input/output of these processing means.

Owing to such a construction, either one of the first signal processing means SP1 and the second signal processing means SP2 is selected, and the input terminal of the thus-selected processing means is connected to the detector 20L while the output terminal of the same processing means is connected to the controller 32.

It is hence possible to most suitably perform the detection of foreign substances on a patterned sample and the detection of foreign substances on a mirror-finished surface by a single apparatus. In this case, it is more preferable to construct some of the elements of the optical system in such a way that those suitable to the former detection and those appropriate for the latter detection can be changed over depending which detections is performed.

In each of the above embodiments, analog comparators having a dividing function were used as analog comparators. This invention is however not limited to the use of such analog comparators. Any analog comparators can however be used in the present invention in so far as they can perform highlighting processing for foreign substances. For example, analog comparators having a subtracting function can also be used.

The vertical illumination beam was irradiated along the optical path in the above embodiments. It may however be irradiated at an angle somewhat deviated from the optical path as long as the objects of the present invention can be attained.

Each of the above-described embodiments of the present invention has brought about the advantages that detection of fine foreign substances present on an object can be performed stably with high sensitivity while still assuring high-speed performance of the detection of the foreign substances.

The present invention has also brought about the advantage that a method for performing high-speed detection of fine foreign substances of about 0.5 $\mu$m on a patterned object in distinction from the pattern on the object and a method for performing high-speed detection of fine foreign substances of about 0.1 $\mu$m on a mirror-finished surface can be practiced by a single apparatus.

A description will next be made of a sixth embodiment of the present invention.

Figure 31:
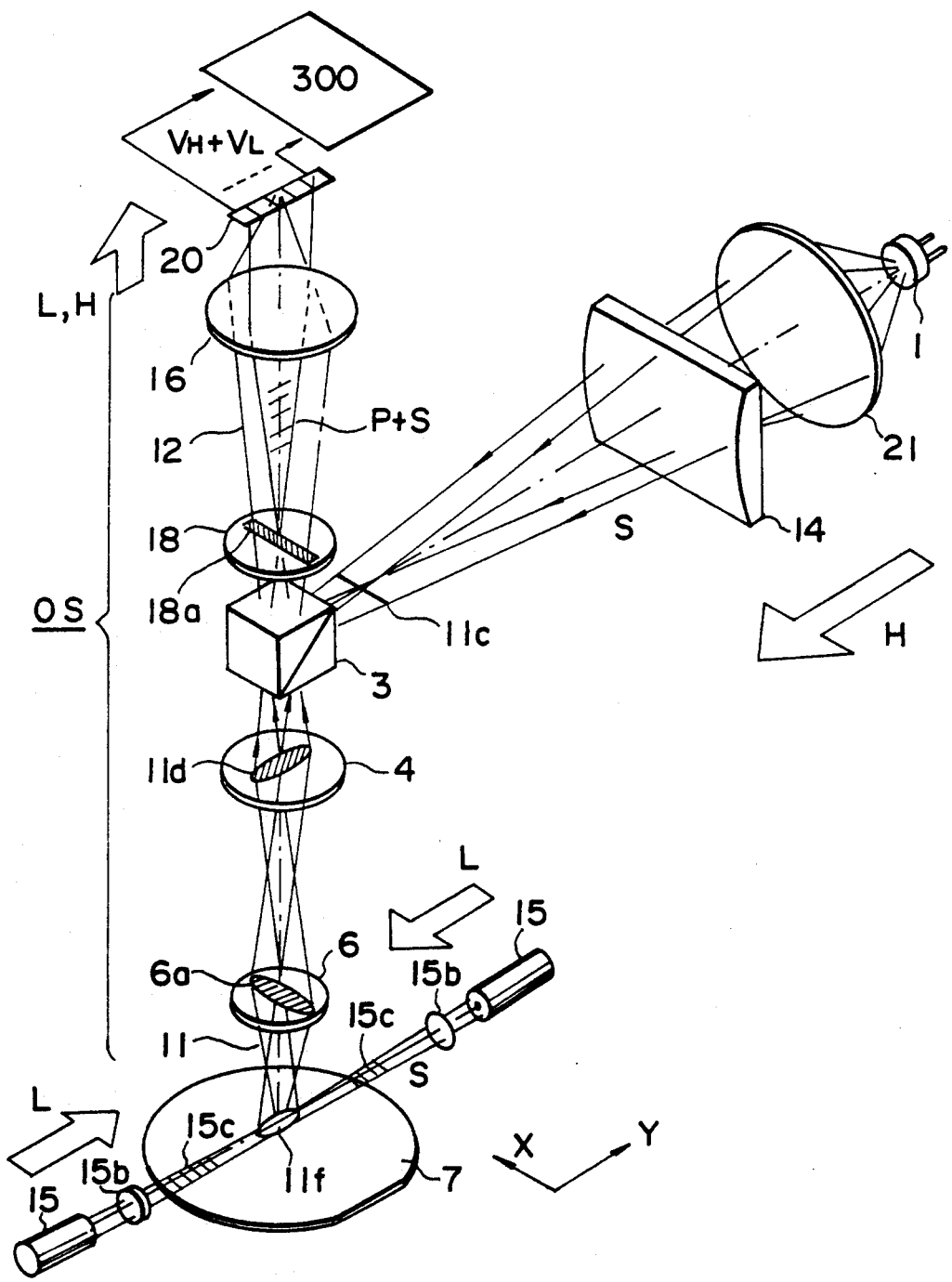
FIG. 31 is a perspective view of an illumination and detection system, showing a sixth embodiment of the present invention.

FIG. 31 is a perspective view of illumination and detection systems, illustrating the sixth embodiment of the method and apparatus of the present invention for the detection of foreign substances. In FIG. 31, each oblique illumination system L adapted to perform oblique illumination (the first illumination) against the sample 7 comprises the laser beam source 15 and the condensing lens 15b. The vertical illumination system H for performing linear (slit-like) vertical illumina-tion against the sample 7 is constructed of the laser beam source 1, the condensing lens 21, the cylindrical lens 14, the semitransparent prism 3, the field lens 4 and the object lens 6. The detections system L(H) is formed of the light shutoff plate 18 having the light shutoff portion 18a for shutting off zeroth-order diffracted light, the imaging lens 16, the one-dimensional solid pickup element array (detector) 20, and a signal processing circuit/signal processor 300.

In the above construction, scanning in Y-direction is obviated as the vertical illumination system H uses the cylindrical lens 14 capable of linearly focusing a laser beam so that the illumination laser beam 11 can be condensed in the form of the linear spot 11f on the sample 7. When the laser beam 11 travelled from the laser beam source 1 and through the condensing lens 21 has passed through the cylindrical lens 14, the linear laser spot 11c is formed. The laser beam 11 which has been reflected by the semitransparent prism 3 forms the linear spot 11d in the diaphragm 4a of the field lens 4 (see FIG. 32) and a linear spot in the diaphragm 6a of the object lens 6 (see FIG. 32). After passage through the object lens 6, the linear spot 11f is condensed on the sample 7. Reflected lights produced as a result of illumination by the illumination systems L,H pass through the object lens 6, semitransparent prism 3 and light shutoff plate 18 and form images on the detector 20 by way of the imaging lens 16. These oblique illumination (the first illumination) and vertical illumination (the second illumination) are performed in a time-sharing pulsated manner. By synchronously detecting the outputs $V_L$, $V_H$ from the detector 20, the scattered lights by the two types of illumination beams can be separated and detected.

Figure 32:
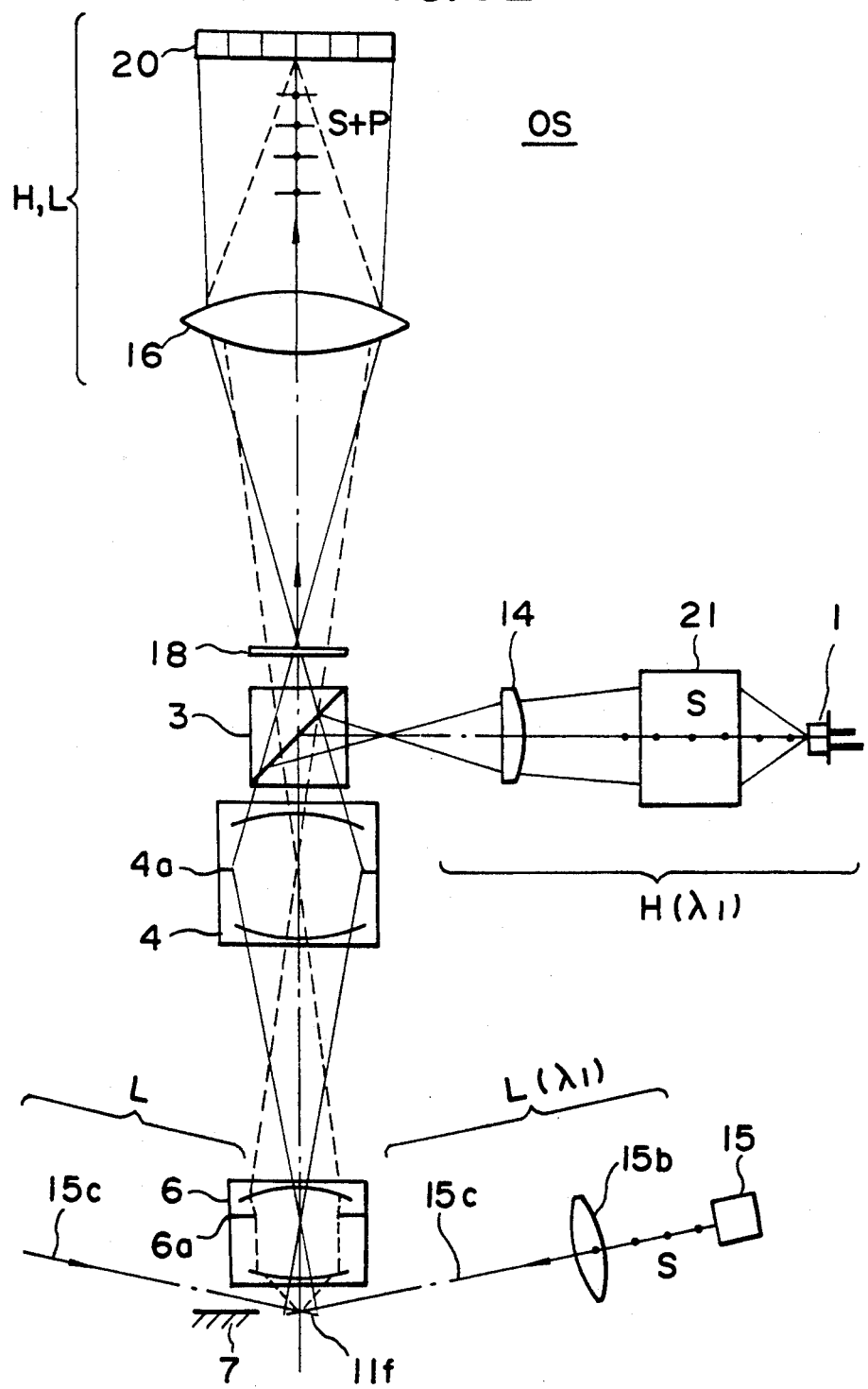
FIG. 32 is an optical path diagram of the state of polarization in the illumination and detection system of FIG. 31.

FIGS. 32-35 are optical path diagrams of polarization states in illumination and detection system, illustrating still further embodiments of the method and apparatus of this invention for the detection of foreign substances. FIG. 32 is an optical diagram of the sixth embodiment of the present invention illustrated in FIG. 31. The state of polarization of each of the illumination beam 11 and scattered light 12 in FIG. 31 will now be described with reference to FIG. 32. The oblique illumination system L and vertical illumination system H are both of S polarization (i.e., linear polarization having oscillation components in X direction). Accordingly, the scattered light 12 from each of the foreign substances and pattern on the surface of the sample 7 is a mixture of P-polarized light (linear polarization having oscillation components in Y direction) and S-polarized light. The whole scattered light (S-polarized light + P-polarized light) is detected by the detector 20 in this embodiment, the quantity of the scattered light detected is high and the detection can be performed at high S/N ratio. High-speed inspection is therefore feasible.

Figure 33:
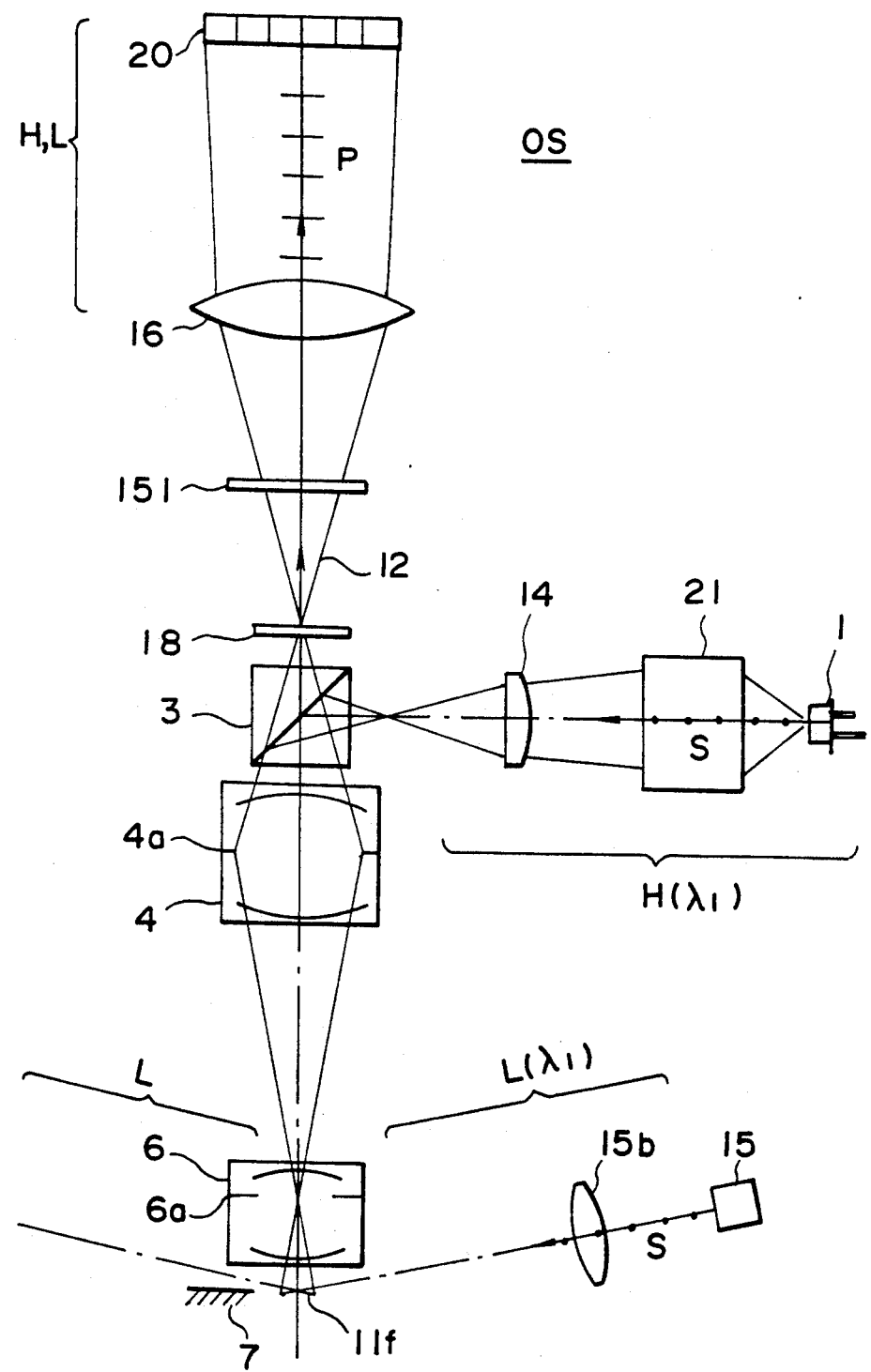
FIG. 33 through FIG. 35 are optical path diagrams showing the states of polarization in the illumination and detection systems of FIG. 7 through FIG. 9, respectively.
Figure 34:
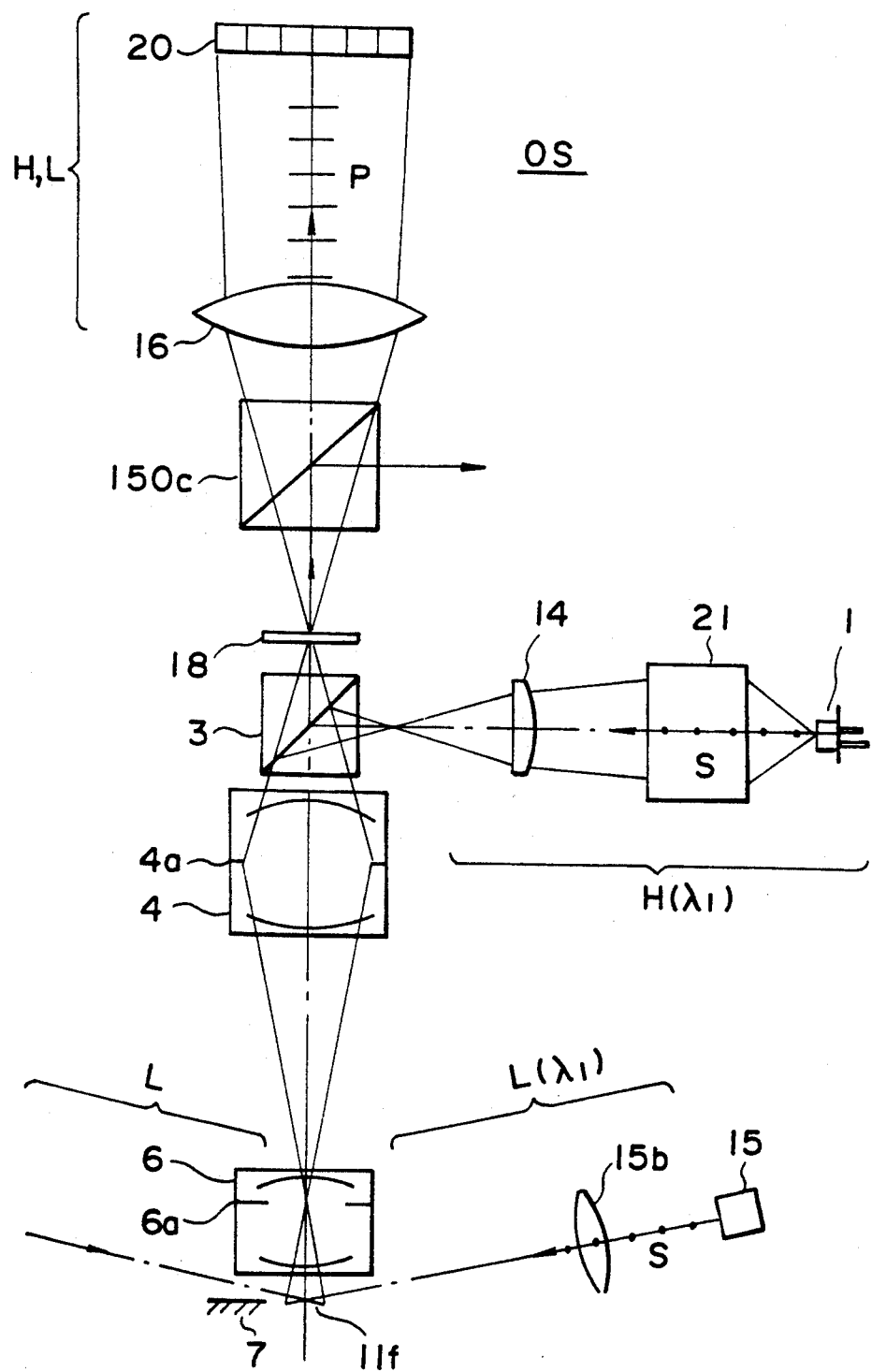
Figure 35:
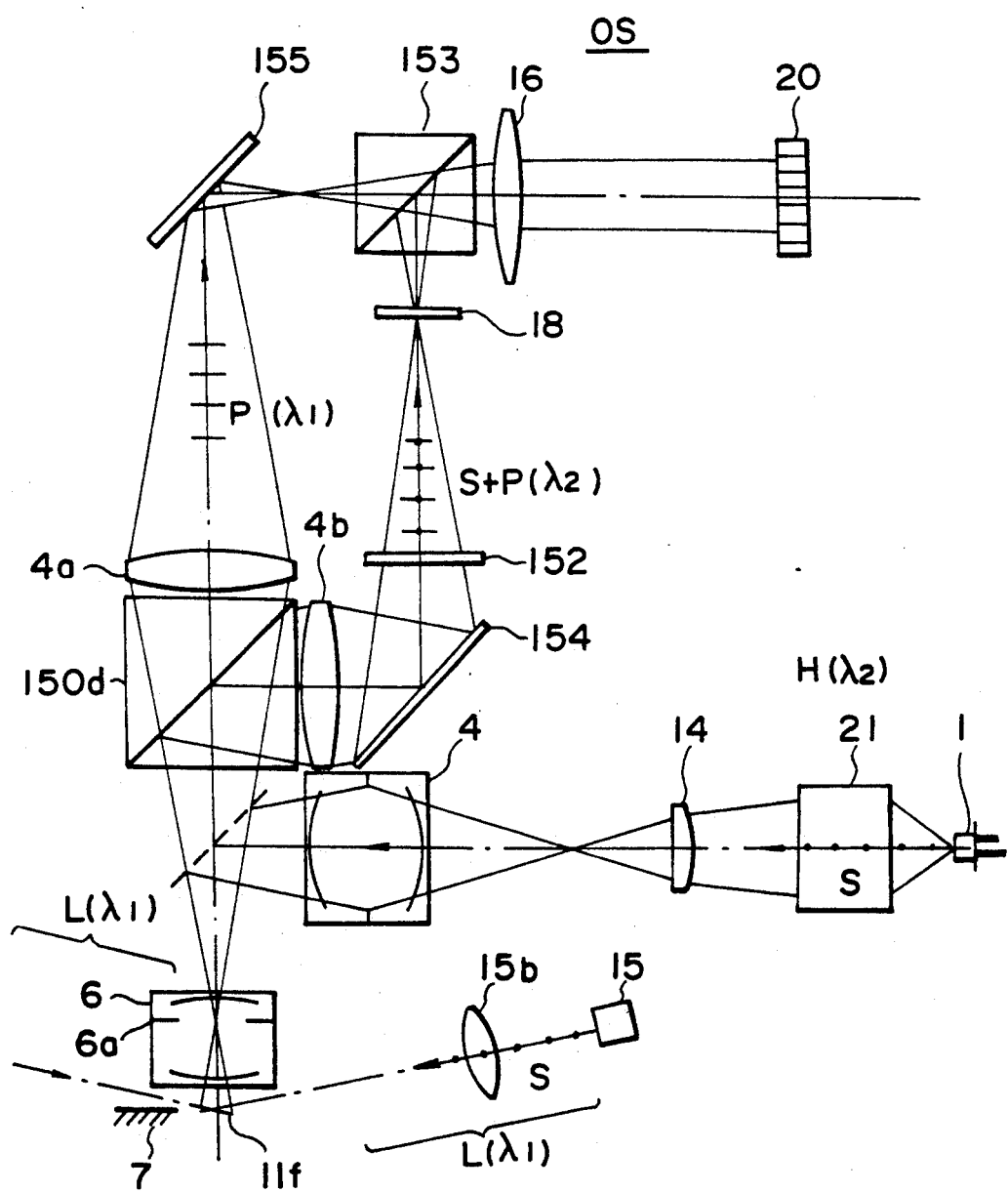

FIGS. 33 through 35 show seventh to ninth embodiments of the present invention. In these embodiments, the discrimination ratio between foreign substances and an associated pattern has been improved over the embodiment of FIG. 31 (FIG. 32). In the seventh embodiment shown in FIG. 33, a deflecting element 151 such as an analyser is arranged in the detection system H. The deflecting element 151 makes it possible to detect only P-polarized light component out of the scattered light 11, so that the discrimination ratio between the substances and the pattern can be improved. In the eighth embodiment of FIG. 34, a polarization beam splitter 150a is used instead of the deflecting element 151 in FIG. 33. The polarization beam splitter 150a has higher transmittance for P-polarized light than the analyser, so that more light can be detected than the embodiment of FIG. 33 and detection can be performed at higher S/N ratio.

In the ninth embodiment of FIG. 35, different wavelengths $\lambda_1$, $\lambda_2$ are used in the oblique illumination system L and vertical illumination system H. In addition, a dichroic mirror 150d having color separation and polarization characteristics is employed. By using the color filter 152 in combination, reflected lights corresponding to the illumination systems L,H can be separated from each other. Since the light shutoff plate 18 is arranged only on the side of the detection system for the scattered light ($\lambda_2$) corresponding to the vertical illumination system H, the scattered light ($\lambda_1$) corresponding to the oblique illumination system L can be detected in a large quantity. The scattered light which has been branched out through the dichroic mirror 150d advances through the mirrors 154,155 and the semitransparent prism 153 and enters the detector 20. This embodiment can also realize an improved discrimination ratio between foreign substances and an associated pattern.

Figure 36A:
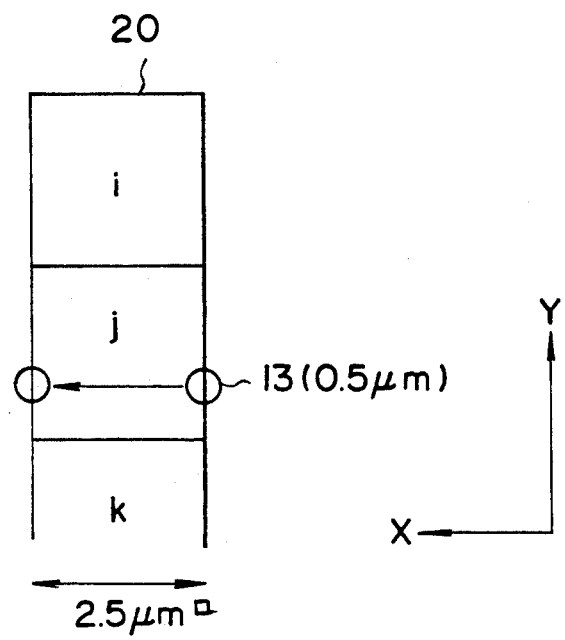
FIG. 36A through FIG. 36C are timing charts of illumination by the laser beam sources in FIG. 31 through FIG. 35, respectively.
Figure 36B:
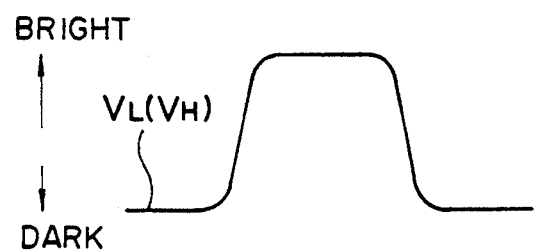
Figure 36C:
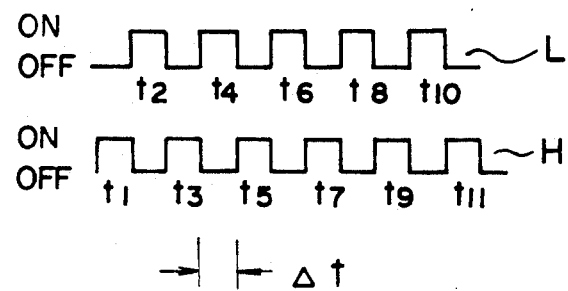

FIGS. 36A through 36C are emission timing charts of the laser beams in FIGS. 31 through 35. In each of the embodiments shown in FIGS. 31 through 35, the oblique illumination and the vertical illumination are performed in a time-sharing pulsated manner and the outputs $V_L$, $V_H$ from the detector 20 are synchronously detected, so that both scattered lights are separated and detected. In FIG. 36A, a fine foreign substance 13 of about 0.5 μm has passed over the detector 20 in which the size of each pixel is 2.5 μm square (when converted to the size on the surface of the sample). FIG. 36B shows variations in the light quantity of the scattered light as measured by the signal $V_L(V_H)$. FIG. 36C shows timings at which the oblique illumination L and vertical illumination H are effected in a time-sharing manner. Their timings are set such that the illuminations L,H are shifted in timing and are alternately performed so as to avoid overlapping. Since the interval Δt between these timings is short, semiconductor lasers permitting high-speed drive are suitable as the laser beam sources 15,1.

Figures 37A, 37B:
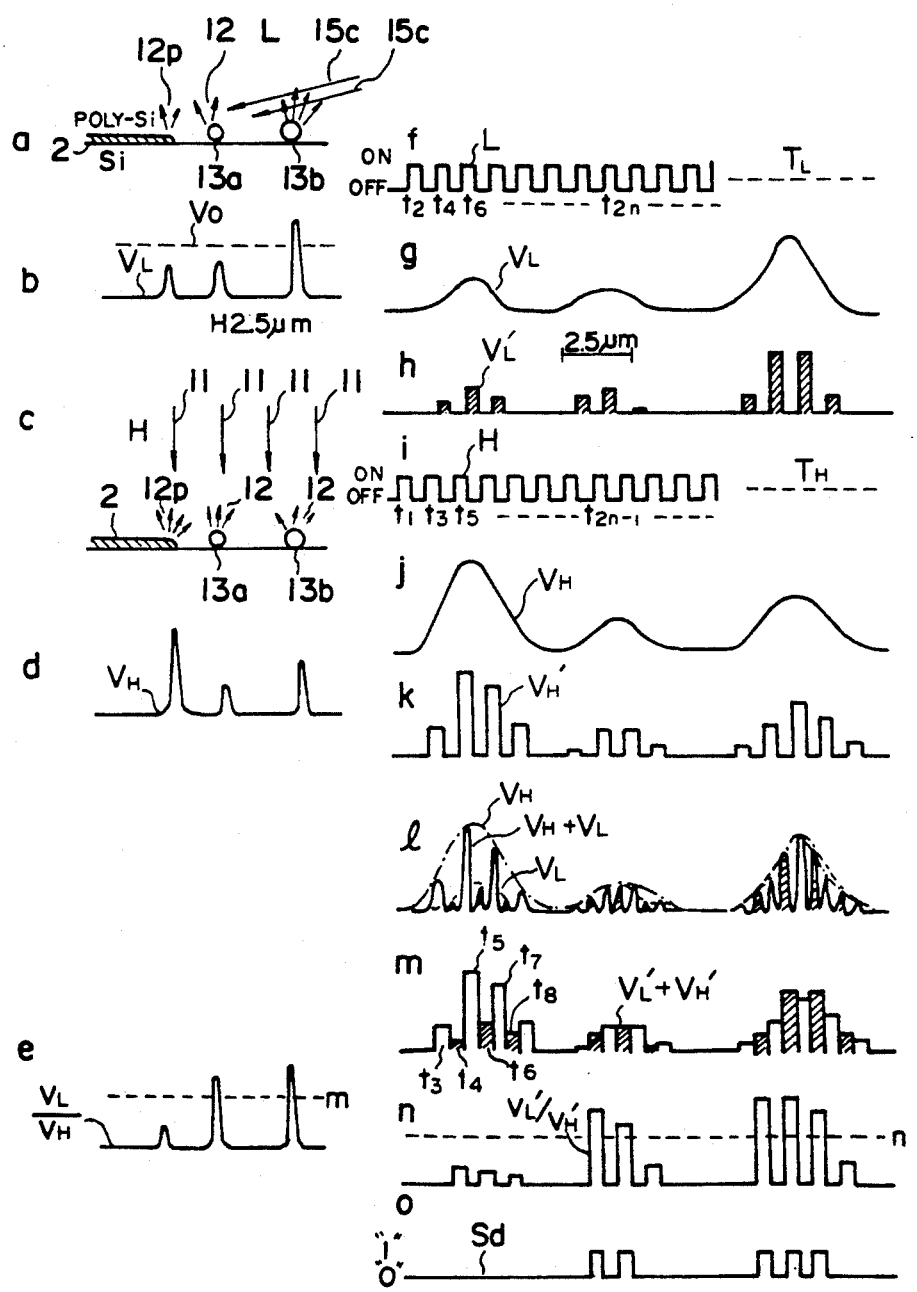
FIG. 37A and FIG. 37B are timing charts of illumination and detection in FIG. 31 through FIG. 35.

FIGS. 37A and 37B are emission and detection timing charts in the respective embodiments, respectively. In FIGS. 37Aa through 37Ae, two illuminations are performed at the same time and continuously. In FIG. 37Aa, oblique illumination laser 15c is irradiated, for example, onto an Si wafer on which there are a pattern 2 and foreign substances 13a,13b. FIG. 37Ab shows output signals $V_L$ at that time. In FIG. 37Ac, the vertical illumination laser 11 is irradiated onto the same spot. FIG. 37Ad illustrates output signals $V_H$ at that time. FIG. 37Ae shows the ratios of the two types of output signals, $V_L/V_H$.

In FIGS. 37Bf through 37Bo, the two types of illuminations are performed in a time-sharing pulsated manner. FIG. 37Bf shows the emission timing of the oblique illumination 15c, FIG. 37Bg output signals $V_L$ when the oblique illumination 15c is effected continuously, and FIG. 37Bh output signals $V'_L$ when the oblique illumination 15c was effected at the emission timing. FIG. 37Bi illustrates the emission timing of the vertical illumination 11. FIG. 37Bj depicts output signals $V_H$ when the oblique illumination 15c was performed continuously, and FIG. 37Bk output signals $V'_H$ when illuminated at the emission timing. FIG. 37Bl shows output signals $V'_L + V'_H$ from the detector 20 when illuminated at the emission timing, and FIG. 37Bm signals obtained after processing the output signals $V'_L + V'_H$ by a sample and hold. FIG. 37Bn illustrates signal ratios $V'_L + V'_H$ obtained by using the sample-and-hold signals, and FIG. 37Bo foreign substance signals Sc obtained by converting the signals $V'_L + V'_H$ to binary signals.

Figure 38:
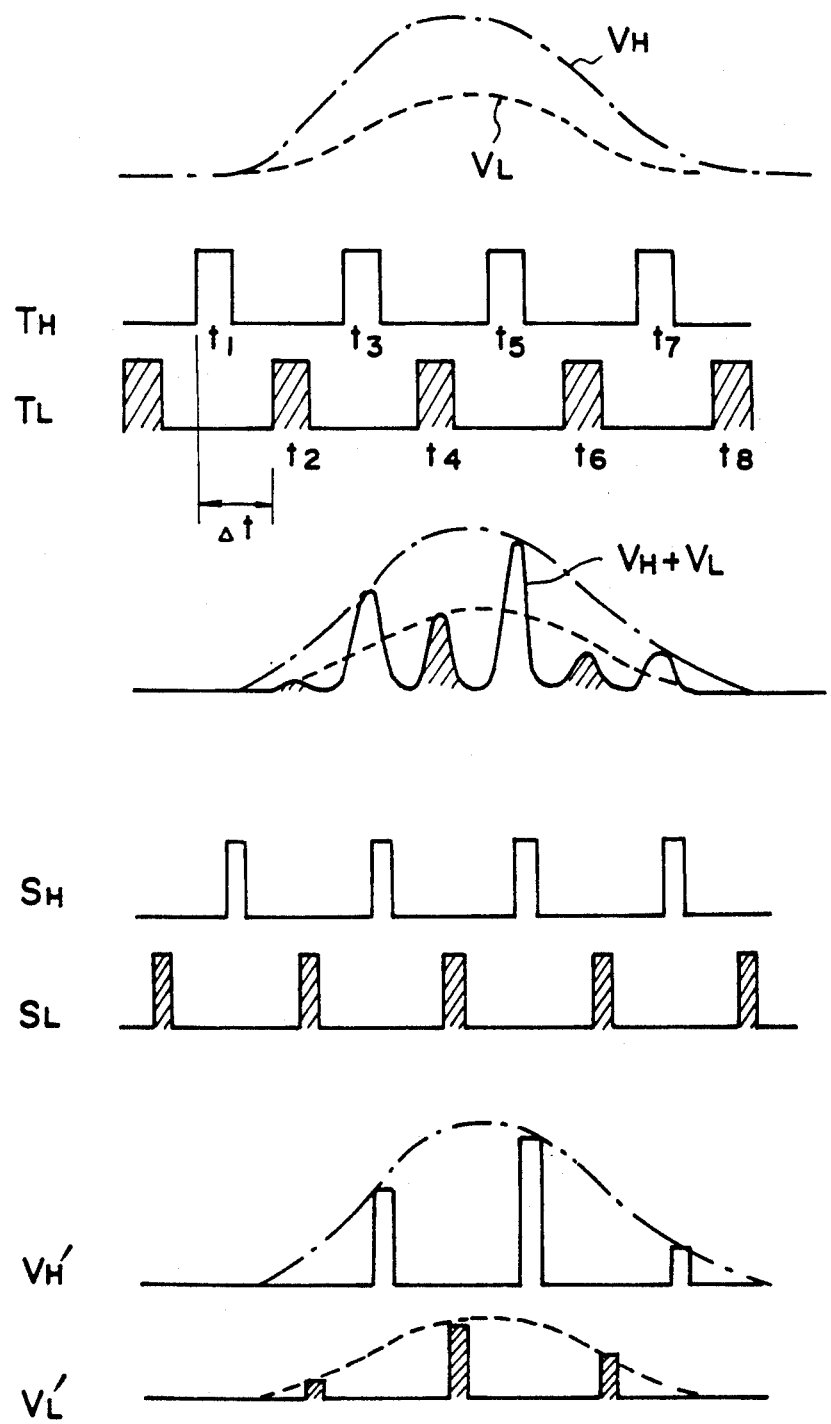
FIG. 38 is timing duty charts of illumination and detection in the respective embodiments shown in FIG. 31 through FIG. 35.

FIG. 38 are timing duty charts of illumination and detection in the embodiments shown in FIG. 31 through FIG. 35. Since an electrical delay generally takes place at the detector 20 or signal processing circuit 300, it is necessary to control the duties of the emission timings $T_L$, $T_H$ below 50% in order to accurately detect scattered lights, which are produced as a result of illustration by the two types of illuminations L, H, and to obtain the output signals $V_L$, $V_H$. By conducting sample and hold of the output signals $V_L + V_H$ in accordance with sampling pulses $S_L$, $S_H$ which are in unison with the emission timings $T_L$, $T_H$, output signals $V'_L$, $V'_H$ can be obtained.

Figure 39:
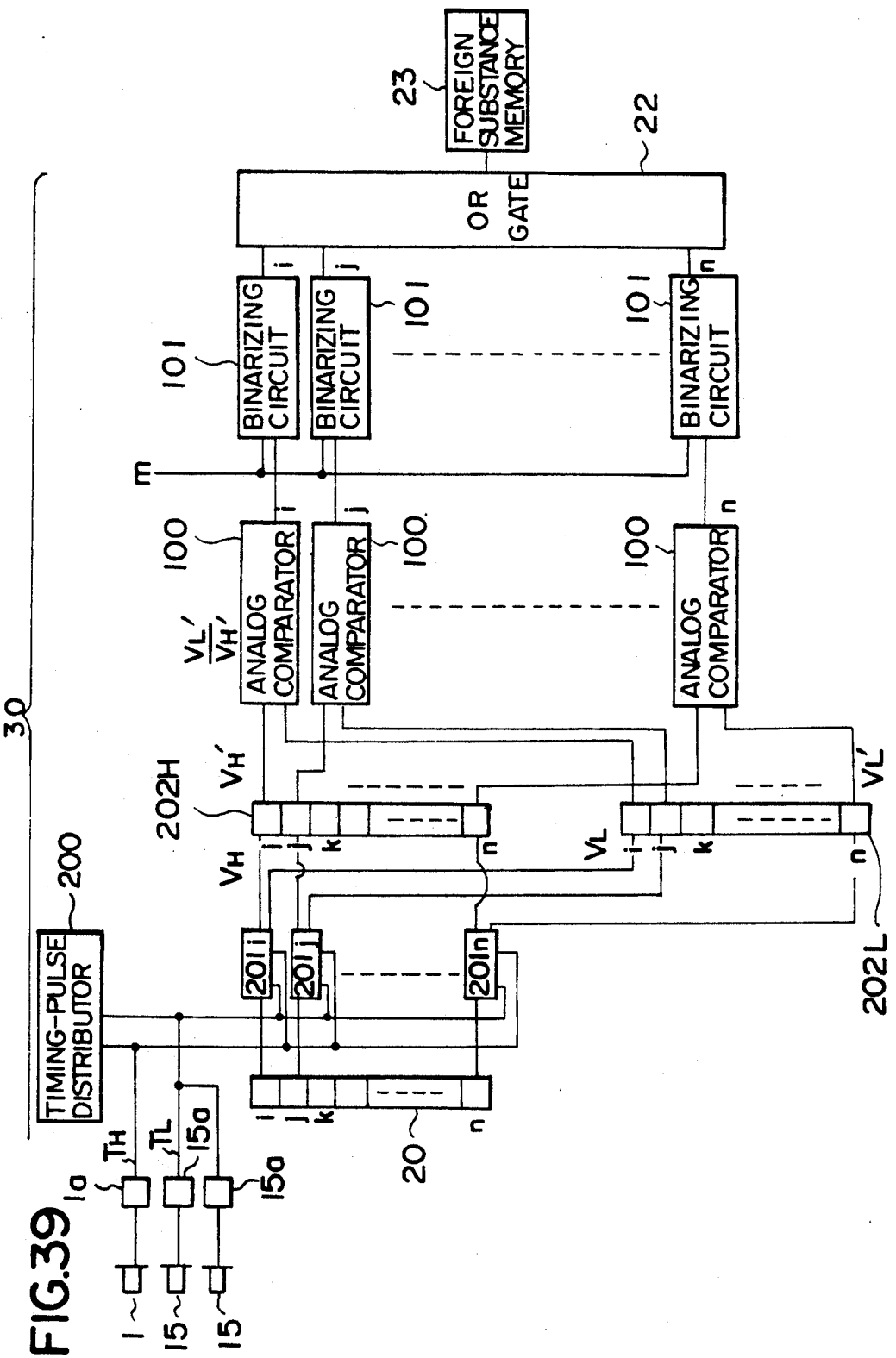
FIG. 39 is a block diagram of a driver and signal processing circuit used in a tenth embodiment of the present invention.

FIG. 39 is a block diagram of driver and signal processing circuit used in a tenth embodiment of the method and apparatus of the present invention for the detection of foreign substances.

In FIG. 39, a timing-pulse distributor 200 provides laser drivers 15a,1a with laser emission timing pulses $T_L$, $T_H$, whereby the laser beams 15,1 are caused to emit in a time-sharing manner. The timing pulses $T_L$, $T_H$ are also delivered to signal separators 201 at the same time, so that the detection signals from the detector 20 are divided into the output signals $V_L$, $V_H$. The scattered light signals $V'_L$ produced at the oblique illumination timing $T_L$ are held in a holding circuit 202L, whereas the scattered light signals $V'_H$ produced at the vertical illumination timing $T_H$ are held in a holding circuit 202H. From the scattered light signals $V'_L$, $V'_H$, signal ratios $V'_L/V'_H$ are calculated at the corresponding analog comparators 100. Upon conversion of these signal ratios to binary signals with respect to the threshold value m at the respective binarizing circuits 101, signals indicative of the detection of the foreign substances 13 can be obtained. By using the plural analog comparators 100 and binarizing circuits 101 in association with the pixels i-n of the detector 20 and performing concurrent processing operations, high-speed and high-sensitivity detection of foreign substances are feasible. The OR gate 22 outputs a foreign substance signal detected by any of the pixels i-n of the detector 20, which is then stored in the foreign substance memory 23.

Figure 40:
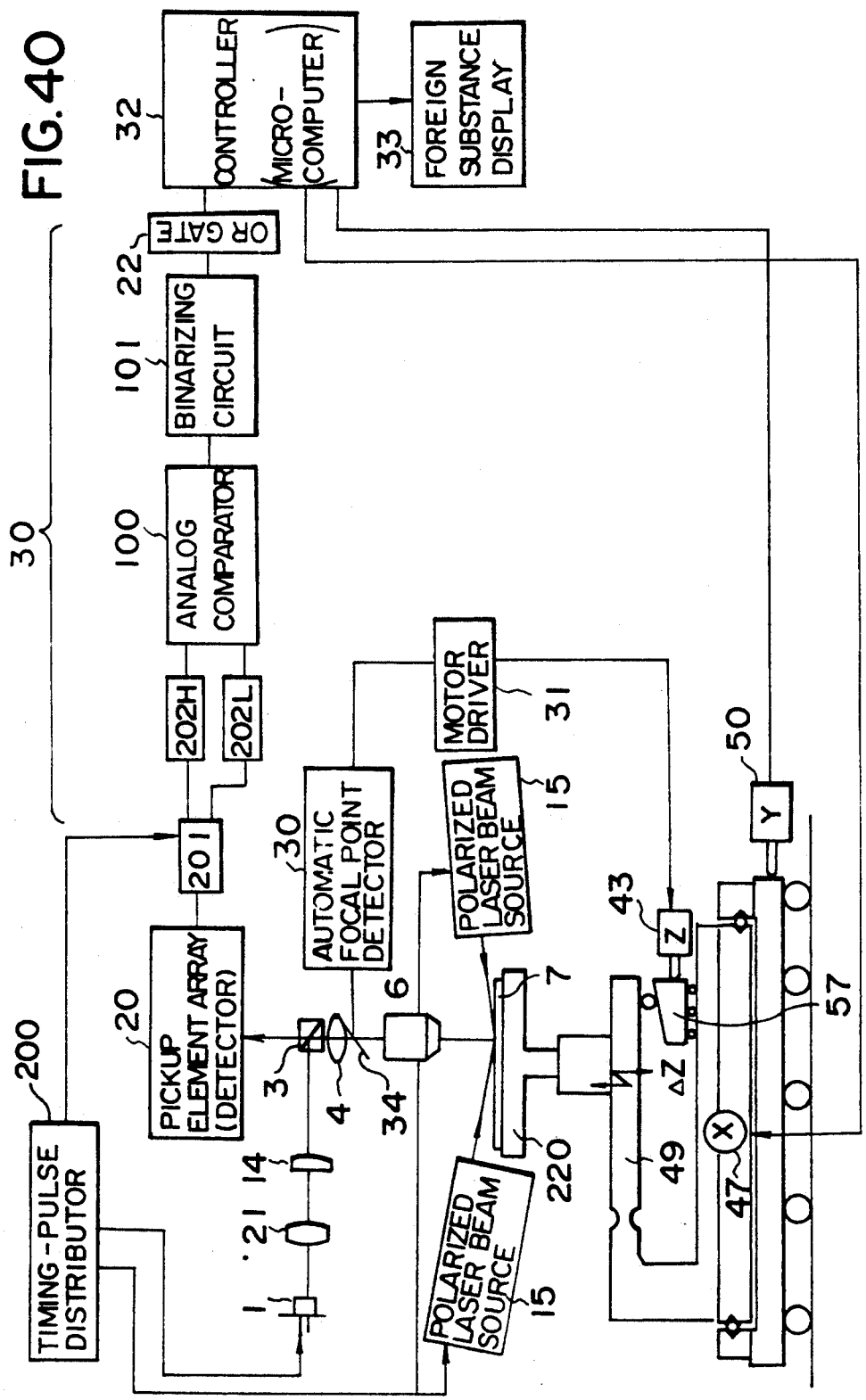
FIG. 40 is a block diagram showing an eleventh embodiment of the present invention.
Figure 41:
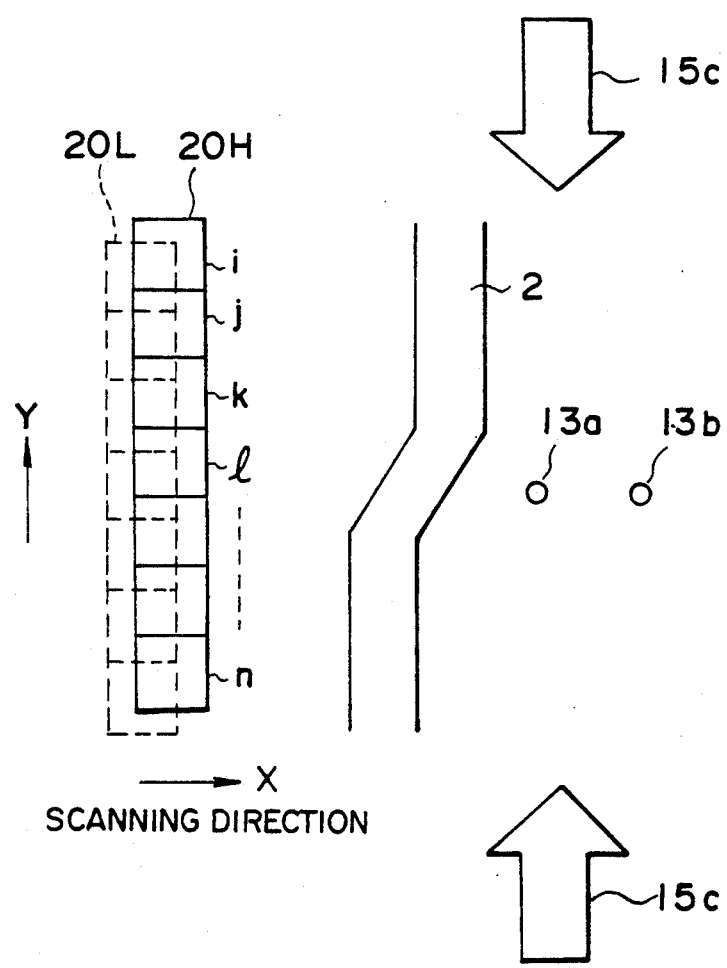
FIG. 41 schematically shows the problem of positional mismatching between two detectors.

FIG. 40 is a block diagram showing an eleventh embodiment of the method and apparatus of the present invention for the detection of foreign substances. In FIG. 40, the sample 7 is fixed on the feed stage 220 and can be moved in X-Y direction by the motor 47 and motor 50. The feed stage 220 is supported by way of the leaf spring 49 and can be moved in the vertical direction ($\Delta Z$) by the motor 43. In addition, the height of the surface of the sample is measured by the automatic focusing sensor 30 and the motor 43 is driven by the motor driver 31, so that $\Delta Z$ is controlled to bring the surface of the sample into registration with the position of the focal point of the object lens 6. The controller 32 controls the motors 47,50 to drive the feed stage 220 such that the entire surface of the sample can be inspected. The controller 32 also outputs each output signal from the OR gate 22 of the signal processing circuit 30 to the foreign substance display 33.

In the eleventh embodiment, the analog comparator 202 is used. By subjecting, to A/D conversion, outputs from the pixels i-n of the detector 30, holding, comparison and conversion to binary signals can also be performed by a digital comparator. The eleventh embodiment has made it possible to use only one detection circuit, so that any deterioration in the sensitivity of foreign substance detection due to a positioning error can be obviated. Further, the use of the single detection circuit has made it possible to reduce the size of a circuit such as an analog amplifier.

The eleventh embodiment of this invention has the advantage that detection of fine foreign substances present on an object such as a patterned wafer can be performed stably with high sensitivity while still assuring high-speed performance of the detection of the foreign substances.

We claim:

1. A method of detecting a foreign substance on a patterned object having a plane surface and a raised pattern formed on said plane surface by illuminating said patterned object and detecting via an optical system light reflected by said patterned object to detect said foreign substance in distinction from said raised pattern, comprising the steps of:

applying oblique illumination onto an oblong area of the plane surface of said patterned object having said raised pattern formed thereon in an oblique direction relative to an optical axis of said optical system, and applying vertical illumination vertically onto the oblong area of the plane surface of said patterned object along the optical axis of said optical system;

receiving, via said optical system, light from said oblique illumination reflected and scattered from the oblong area and light from said vertical illumination reflected and scattered from the oblong area, separating the received scattered lights from the received reflected lights by shutting off the received reflected lights, and independently detecting the separated scattered lights with one-dimensional photodetecting means to obtain a first detection signal based on the scattered light from the oblique illumination and a second detection signal based on the scattered light from the vertical illumination, wherein the oblong area is large enough to contain an image of an entire photodetecting area of said one-dimensional photodetecting means projected onto the plane surface of said patterned object through said optical system; and non-additively processing said first detection signal and said second detection signal to cancel a component of said first detection signal and said second detection signal due to light scattered from said raised pattern and detect said foreign substance.

2. A method according to claim 1, wherein said oblique illumination and said vertical illumination have mutually different polarizations.

3. A method according to claim 1, wherein the step of non-additively processing said first detection signal and said second detection signal includes the steps of obtaining a ratio of said first detection signal and said second detection signal, comparing the ratio with a predetermined reference value, and detecting the presence of the foreign substance depending upon whether or not the ratio exceeds the predetermined reference value.

4. A method according to claim 1, wherein said oblique and vertical illuminations have mutually different wavelengths, and the separated scattered lights are separated from each other according to their wavelengths and are independently detected by said photodetecting means.

5. A method according to claim 1, wherein said oblique and vertical illuminations are applied in a time-sharing manner, and the separated scattered lights are detected by said photodetecting means in a time-sharing manner in synchronism with the time-sharing of said oblique and vertical illuminations such that the first and second detection signals are obtained independently.

6. A method of detecting a foreign substance on an unpatterned object having an unpatterned mirror-finished surface by illuminating said unpatterned object and detecting via an optical system light reflected by said unpatterned object to detect said foreign substance on said unpatterned mirror-finished surface of said unpatterned object, comprising the steps of:

applying oblique illumination onto an oblong area of the unpatterned mirror-finished surface of said unpatterned object in an oblique direction relative to an optical axis of said optical system, and applying vertical illumination vertically onto the oblong area of the unpatterned mirror-finished surface of said unpatterned object along the optical axis of said optical system;

receiving, via said optical system, light from said oblique illumination reflected and scattered from the oblong area, and light from said vertical illumination reflected and scattered from the oblong area, separating the received scattered lights from the received reflected lights, and detecting the separated scattered lights with one-dimensional photodetecting means to obtain a first detection signal based on the scattered light from the oblique illumination and a second detection signal based on the scattered light from the vertical illumination, wherein the oblong area is large enough to contain an image of an entire photodetecting area of said one-dimensional photodetecting means projected onto the unpatterned mirror-finished surface of said unpatterned object through said optical system; and additively processing said first detection signal and said second detection signal to detect said foreign substance.

7. A method of detecting a foreign substance on an object by illuminating said object and detecting via an optical system light reflected by said object to detect said foreign substance, comprising the steps of:

applying oblique illumination onto said object in an oblique direction relative to an optical axis of said optical system and vertical illumination vertically onto said object along the optical axis of said optical system;

condensing via said optical system lights scattered by said object from said oblique and vertical illuminations, and independently detecting the condensed scattered lights with photodetecting means to obtain a first detection signal based on the scattered light from the oblique illumination and a second detection signal based on the scattered light from the vertical illumination;

when the object has a plane surface and a raised pattern formed on said plane surface, detecting the foreign substance on the basis of a difference between the first and second detection signals; and when the object has a mirror-finished surface, detecting the foreign substance by adding together the first and second detection signals to obtain a sum and comparing the sum with a predetermined reference value.

8. An apparatus for detecting a foreign substance on a patterned object having a plane surface and a raised pattern formed on said plane surface by illuminating said patterned object and detecting via an optical system light reflected by said patterned object to detect said foreign substance in distinction from said raised pattern comprising:

an optical system;

oblique illumination means for applying oblique illumination onto an oblong area of the plane surface of said patterned object having said raised pattern formed thereon in an oblique direction relative to an optical axis of said optical system;

vertical illumination means for applying vertical illumination vertically onto the oblong area of the plane surface of said patterned object along the optical axis of said optical system;

means for receiving, via said optical system, light from said oblique illumination reflected and scattered from the oblong area and light from said vertical illumination reflected and scattered from the oblong area;

means for separating the received scattered lights from the received reflected lights by shutting off the received reflected lights;

one-dimensional photodetecting means for independently detecting the separated scattered lights to obtain a first detection signal based on the scattered light from the oblique illumination and a second detection signal based on the scattered light from the vertical illumination, wherein the oblong area is large enough to contain an image of an entire photodetecting area of said one-dimensional photodetecting means projected onto the plane surface of said patterned object through said optical system; and signal processing means for non-additively processing said first detection signal and said second detection signal to cancel a component of said first detection signal and said second detection signal due to light scattered from said raised pattern and detect said foreign substance.

9. An apparatus according to claim 8, wherein said oblique illumination and said vertical illumination have mutually different polarizations, wherein said one-dimensional photodetecting means includes a polarization beam splitter for separating the scattered light from the oblique illumination and the scattered light from the vertical illumination from each other according to their mutually different polarizations, and wherein said one-dimensional photodetecting means independently detects the scattered lights separated from each other according to their mutually different polarizations.

10. An apparatus according to claim 8, wherein said separating means includes shutoff means for preventing zeroth-order diffracted light in light reflected from the oblong area from being incident to the one-dimensional photodetecting means.

11. An apparatus according to claim 8, wherein said one-dimensional photodetecting means includes one-dimensional solid pickup means in which plural pixels are arranged linearly, wherein said vertical illumination means includes a cylindrical lens for applying a linear light beam onto the oblong area along the optical axis of said optical system as said vertical illumination, and wherein the oblong area is large enough to contain an image of an entire photodetecting area of said one-dimensional solid pickup means projected onto the plane surface of said patterned object through said optical system.

12. An apparatus according to claim 8, wherein said oblique and vertical illuminations have mutually different wavelengths, wherein said one-dimensional photodetecting means includes means for separating the scattered light from said vertical illumination and the scattered light from said oblique illumination from each other according to their mutually different wavelengths, and a first one-dimensional photodetecting element and a second one-dimensional photodetecting element for independently detecting the scattered lights separated from each other according to their mutually different wavelengths.

13. An apparatus according to claim 12, wherein the signal processing means includes a division comparator for obtaining a ratio of the first detection signal and the second detection signal to cancel the component of the first detection signal and the second detection signal due to the light scattered from the raised pattern, and a binarizing circuit for converting the ratio to a binary signal with respect to a predetermined threshold value to detect the foreign substance depending on whether or not the ratio exceeds the predetermined threshold value.

14. An apparatus according to claim 12, wherein the signal processing means includes a subtracter for obtaining a difference between the first detection signal and the second detection signal to cancel the component of the first detection signal and the second detection signal due to the light scattered from the raised pattern, and a binarizing circuit for converting the difference to a binary signal with respect to a predetermined threshold value to detect the foreign substance depending on whether or not the difference exceeds the predetermined threshold value.

15. An apparatus according to claim 12, wherein the means for separating the scattered lights from each other according to their mutually different wavelengths includes a color-separation element for separating the scattered lights from each other according to their mutually different wavelengths.

16. An apparatus according to claim 15, wherein the color-seperation element is selected from the group consisting of a color-separation prism, a combination of a semitransparent mirror and a color filter, a combination of a dichroic mirror and a color filter, and a dichroic mirror prism.

17. An apparatus according to claim 8, wherein said oblique and vertical illumination means are operated in a time-sharing manner, wherein said one-dimensional photodetecting means detects the first and second detection signals in a time-sharing manner corresponding to the oblique and vertical illuminations, respectively, and wherein said signal processing means includes means for storing and holding one of the first detection signal and the second detection signal while the other one of the first detection signal and the second detection signal is detected such that the first detection signal and the second detection signal are available at the same time.

18. An apparatus according to claim 17, wherein the signal processing means includes a division comparator for obtaining a ratio of the first detection signal and the second detection signal to cancel the component of the first detection signal and the second detection signal due to the light scattered from the raised pattern, and a binarizing circuit for converting the ratio to a binary signal with respect to a predetermined threshold value to detect the foreign substance depending on whether or not the ratio exceeds the predetermined threshold value.

19. An apparatus according to claim 17, wherein the signal processing means includes a subtracter for obtaining a difference between the first detection signal and the second detection signal to cancel the component of the first detection signal and the second detection signal due to the light scattered from the raised pattern, and a binarizing circuit for converting the difference to a binary signal with respect to a predetermined threshold value to detect the foreign substance depending on whether or not the difference exceeds the predetermined threshold value.

20. An apparatus for optically detecting a foreign substance on an object, comprising:
   an objective lens;
   oblique illumination means for applying oblique illumination onto said object in an oblique direction relative to an optical axis of said objective system;
   vertical illumination means for applying vertical illumination vertically onto said object via said objective lens along the optical axis of said objective lens;
   an optical system for condensing light scattered by said object;
   signal detecting means responsive to the condensed scattered light from said optical system for independently detecting lights scattered by said object from said oblique and vertical illuminations to obtain a first detection signal based on the scattered light from the oblique illumination and a second detection signal based on the scattered light from the vertical illumination;
   first signal processing means for detecting the foreign substance on the basis of a difference obtained by comparing the first and second detection signals with each other;
   second signal processing means for detecting the foreign substance on the basis of a sum obtained by adding together the first and second detection signals; and
   means for selecting the first signal processing means when detecting a foreign substance on an object having a plane surface and a raised pattern formed on said plane surface, and for selecting the second signal processing means when detecting a foreign substance on an object having a mirror-finished surface.

21. An apparatus for detecting a foreign substance on an unpatterned object having an unpatterned mirror-finished surface by illuminating said unpatterned object and detecting via an optical system light reflected by said unpatterned object to detect said foreign substance on said unpatterned mirror-finished surface of said unpatterned object comprising:

an optical system;

oblique illumination means for applying oblique illumination onto an oblong area of the unpatterned mirror-finished surface of said unpatterned object in an oblique direction relative to an optical axis of said optical system;

vertical illumination means for applying vertical illumination vertically onto the oblong area of the unpatterned mirror-finished surface of said unpatterned object along the optical axis of said optical system;

means for receiving, via said optical system, light from said oblique illumination reflected and scattered from the oblong area and light from said vertical illumination reflected and scattered from the oblong area;

means for separating the received scattered lights from the received reflected lights by shutting off the received reflected lights;

one-dimensional photodetecting means for detecting the separated scattered lights to obtain a first detection signal based on the scattered light from the oblique illumination and a second detection signal based on the scattered light from the vertical illumination, wherein the oblong area is large enough to contain an image of an entire photodetecting area of said one-dimensional photodetecting means projected onto the plane surface of said patterned object through said optical system; and signal processing means for additively processing the first detection signal and the second detection signal to detect the foreign substance.

* * * * *